United States Patent
Stewart (12)

(10) Patent No.: US 6,482,406 B1
(45) Date of Patent: *Nov. 19, 2002

(54) CELL-BASED GENE THERAPY FOR THE PULMONARY SYSTEM

(76) Inventor: Duncan J. Stewart, 3 Blythwood Crescent, Toronto, Ontario (CA), M4P 2K2

( * ) Notice: Subject to any disclaimer, the term of this patent is extended or adjusted under 35 U.S.C. 154(b) by 0 days.

This patent is subject to a terminal disclaimer.

(21) Appl. No.: 09/404,652

(22) Filed: Sep. 24, 1999

Related U.S. Application Data

(63) Continuation-in-part of application No. 09/276,654, filed on Mar. 26, 1999.
(51) Int. Cl.$^7$ .......................... A61K 48/00; A01N 43/04; A01N 65/00; C12N 15/74; C12N 5/02
(52) U.S. Cl. ...................... 424/93.21; 514/44; 424/93.1; 435/320.1; 435/325
(58) Field of Search .................... 514/44; 424/93.1, 424/93.21; 435/320.1, 325

(56) References Cited

U.S. PATENT DOCUMENTS

| | | | |
|---|---|---|---|
| 5,219,740 A | 6/1993 | Miller et al. | 435/69.6 |
| 5,658,565 A | 8/1997 | Billiar et al. | 424/93.21 |
| 5,785,965 A | 7/1998 | Pratt | 424/93.21 |
| 5,792,453 A | 8/1998 | Hammond et al. | 424/93.21 |
| 5,830,879 A | 11/1998 | Isner | 514/44 |
| 5,910,488 A | 6/1999 | Nabel et al. | 514/44 |
| 5,916,803 A | 6/1999 | Sedlacek et al. | 435/320.1 |
| 5,941,868 A | 8/1999 | Kaplan et al. | 604/500 |

FOREIGN PATENT DOCUMENTS

| | | |
|---|---|---|
| CA | 2086844 | 7/1994 |
| WO | WO92/15676 | 9/1992 |
| WO | WO93/13807 | 7/1993 |
| WO | W98/19712 | 5/1998 |

OTHER PUBLICATIONS

Ross et al., Gene therapy in the United States: A five-year status report, 1996, Human Gene Therapy, vol. 7, pp. 1781–1790.*

Yano et al., Successful in vivo and ex vivo transfection of pulminary artery segments in lung isografts, 1997, The Journal of Thoracic and Cariovascular Surgery, pp. 793–802.*

Abstract, Journal of American College of Cardiology, Feb. 1998.

Rodman et al., Am. J. Resp. Cell Mol. Biol., vol. 16., 1997, In Vitro Gene Delivery to the Pulmonary Circulation in Rats: Transgene Distribution and Distribution and Vascular Inflammatory Response.

Tuder et al., J. Clin. Invest., vol. 95, 1995, "Increased Gene Expression for VEGF and the VEGF Receptors KDR/FLK and Flt in Lungs Exposed to Acute or to Chronic Hypoxia".

Voelkel et al., "Vascular Endothelial Growth Factor in Pulmonary Hypertension".

Ziche et al., J. Clin. Invest. vol. 99, No. 11, 1997, "Nitric Oxide Synthase Lies Downstream from Vascular Endothelial Growth Factor–induced but not Basic Fibroblast Growth Factor–Induced Angiogenesis".

Lozier et al., JAMA, 1994, vol. 271, No. 1, "Gene Therapy and the Hemophilias".

Junker et al., Blood, vol. 88, No. 12, 1997, "Hematopoietic Potential and Reroviral Transduction of CD34+Thy–1+ Peripheral Blood Stem Cells from Asymptomatic Human Immunodeficiency Virus Type–1—Infected Individuals Mobilized with Granulocyte Colony–Stimulating Factor".

Raper et al., Annals of Surgery, vol. 223, No. 2, 1996, "Safety and Feasibility of Liver–Directed ex vivo Gene Therapy for Homozygous Familial Hypercholesterolemia".

De Backer et al., 1999, "Primary Pulmonary Hypertension with Fatal Outcome in a Young Woman and Review of the Literature".

Wanstall et al., Disease Management, 1998, "Recognition and Management of Pulmonary Hypertension".

Curiel, et al., Am. J. Respic, Cell Mol. Biol., vol. 14, 1996, "Gene Therapy Approaches for Inherited and Acquired Lung Diseases".

McCluski et al., Molecular Medicine, 1999, "Route and Method of Delivery of DNA Vaccine Influence Immune Responses in Mice and Non–Human Primates".

Tzeng et al., Molecular Medicine, vol. 2, No. 2, 1996, "Vascular Gene Transfer of the Human Inducible Nitric Oxide Synthase: Characterization of Activity and Effects on Myointimal Hyperplasia".

Moldawer et al., Shock, vol. 12, No. 2, 1999, "Applications of Gene Therapy to Acute Inflammatory Diseases".

Teichert–Kuliszewska et al., Circ Res, 1998, "Role of Nitric Oxide in the Angiogenic Response in vitro to Basic Fibroblast Growth Factor".

van der Zee et al., Circulation, 1997, "Vascular Endothelial Growth Factor/Vascular Permeability Factor Augments Nitric Oxide Release from Quiescent Rabbit and Human Vascular Endothelium".

(List continued on next page.)

Primary Examiner—Deborah J. Reynolds
Assistant Examiner—Eleanor Sorbello
(74) Attorney, Agent, or Firm—Ridout & Maybee LLP

(57) ABSTRACT

Cell-based gene transfer is effected by administering transfected cells containing an expressible transgene coding for an angiogenic factor or other therapeutic factor, into the pulmonary circulation of a patient, where the cells express and secrete expression products of the transgene to act locally at the site of expression of expression, and in some cases to be conveyed by the patient's circulation to other body organs. The process is especially useful in treatment of pulmonary hypertension by means of expressed angiogenic factors. Also provided is the use of angiogenic factors, delivered by other means than cell-based gene transfer, in treating pulmonary hypertension.

8 Claims, 9 Drawing Sheets

OTHER PUBLICATIONS

Papapetropoulous et al., A. J. Pathol, 1997, "Nitric Oxide Synthase Inhibitors Attenuate Transforming–Growth–Factor–Beta 1–Stimulated Capillary Organization in vitro".

van der Zee et al., Am J. Physiol, 1996, "Vascular Endothelial Growth factor/Vascular Permeability Factor Augments Nitric Oxide Release From Quiescent Rabbit and Human Vascular Endothelium".

Morbidelli et al., Adv Prostaglandin Thomboxane Leukot Res, 1995, "Nitric Oxide Modulates Angiogenesis Elicited by Prostaglandin E1 in Rabbit Cornea".

Feman, Curr Opin Ophthalmol, 1997 "New Discoveries in Diabetes– and Thyroid–Related Eye Disease".

Dunphy et al., Hum Gene Ther., 1999, "Reciprocal Enhancement of Gene Transfer by Combinatorial Adenovirus Transduction and Plasmid DNA Transfection in vitro and in vivo".

Blardi, et al., Drugs Exp Clin Res, 1999, "Stimulation of Endogenous Adenosine Release by Oral Administration of Quercetin and Resveratrol in Man".

Lewis, et al., Cardiovas Res, 1977, "Angiogenesis by gene Therapy: a new horizon for myocardial revascularization".

Diebold et al., Hum Gen Ther, 1999, "Efficient gene delivery into human dendritic cells by adenovirus polyethylenimine and mannose polyehtylenimine transfection".

Chen et al., Cancer Gene Ther, 1995, "A novel nonviral cytoplasmic gene expression system and its implications in cancer gene therapy".

Setoguchi et al., Nippon Rinsho, 1996, "Transfer of endothelial nitric oxide synthase gene in the purpose of gene therapy for pulmonary arterial hypertension".

Falqui et al., J Mol Med, 1999, "Human proinsulin production in primary rat hepatocytes after retroviral vector gene transfer".

Flqui et al., hum Gene Ther, 1999, "Reversal of diabetes in mice by implantation of human fibroblasts genetically engineered to release mature human insulin".

Janssens et al.,J Clin Invest, 1996, "Adenoviral–mediated transfer of the human endothelial nitric oxide synthase gene reduces acute hypoxic pulmonary vasoconstriction in rats".

Symes et al., Ann Thorac Surg, 1999, Gene therapy with vascular endothelial growth factor for inoperable coronary artery disease?.

Falqui et al., Hum Gene Ther, 1999, "Reversal of diabetes in mice by implantation of human fibroblasts genetically enineered to release mature human insulin".

Maches et al., Langenbecks Arch Surg, 1998, "Genetically modified fibroblast induced angiogenesis in the rat epigastric island flap".

Huard et al., Biochem Biphys Res Commun, 1998, "Transplantation of dermal fibroblasts expressing MyoD1 in mouse muscles".

Mazurier et al., J Inherit Metab Dis, 1997, "Gene transfer of uroporphyriogen III synthase cDNA into haematopoietic progenitor cells in view of a future gene therapy in cogenital erythropoietic porphyria".

Chun et al., American Physiological Society, 1996, "Developmental expression of NOS isoforms in fetal rat lung:implications for transitional circulation and pulmonary angiogenesis".

Babie et al., American Heart Association, 1998, "Role of Nitric Oxide in the Angiogenic Response in vitro to basic fibroblast growth factor".

Santibanez et al., Biol Res, 1997, "Construction of a gene encoding the insect bactericidal protein attacin. Studies on its expression in *escherichia coli*".

Ziche et al., J Clin Invest, 1997, "Nitric oxide synthase lies downstream from vascular endothelial growth factor–induced but not basic fibroblast growth factor–induced angiogenesis".

Feman, Curr Opin Ophthalmol, 1997, "New discoveries in diabetes– and thyroid–related eye disease".

Dunphy et al., Hum Gene Ther, 1999, "Reciprocal enhancement of gene transfer by combinatorial adenovirus transduction and plasmid DNA transfection in vitro and in vivo".

Zuidam et al., Int J Pharm., 1999, "Characterization of DNA–lipid complexes commonly for gene delivery".

Yao et al., J Biol Chem, 1999, "The transcription factor EGR–1 supresses transformation of human fibrosarcoma HT1080 cells by coordinated induction of transforming growth factor–beta 1, fibronectin, and plasminogen activator inhibitor–1".

Coonrod et al., Gen Ther, 1997, "On the mechanism of DNA transfection: efficient gene transfer without viruses".

Eserion et al., Biochim Biophys Acta, 1998, "Cationic lipid–mediated gene transfer: effect of serum on cellular uptake and intracellular fate of lipopolyamine/DNA complexes".

Watanabe et al., J Biochem(Tokyo), 1994, "Highly efficient transfection into primarycultured mouse hepatocytes by use of ation–liposomes: an appliation for immunization".

Setoguchi et al., Nippon Rinsho, 1996, "Transfer of endothelialnitric oxide synthase gene in the purpose of gene therapy for pulmonary arterial hypertension".

Curiel et al., Am J Respir Cell Mol Biol, 1996, "Gene therapy approaches for inherited and acquired lun diseases".

Rosengart et al., Circulation, 1999, "Angiogenesis for therapy: phase I assessment of direct intramyocardial administration of an adenovirus vector expressing VEGF121 cDNA to individual with clinically significant severe coronary artery disease".

Kida et al., Nippon Rinsho, 1999, "A new medical treatment for thrombosis by genetic engineering".

Losordo et al., Am Heart J, 1999, "Gene therapy for myocardial angiogenesis".

Isner, Hosp Pract, 1999, "Manipulating angiogenesis against vascular disease".

Kalka et al., Med Klin, 1999, "Vascular endothelial factor (VEGF): therapeutic angiogenesis and vasculogenesis in the treatment of cardiovascular disease".

Lewis et al., Cardiovasc Res, 1997, "Angiogenesis by gene therapy: a new horizon for myocardial revascularization".

Melillo et al., Cardiovasc Res, 1997, "Gene Therapy for collateral vessel development".

Nikol et al., Heart, 1997, "Possible uses of gene therapy in reducing coronary restenosis".

Tsurumi et al., Circulation, 1997, "Treatment of acute limb ischemia by intramuscular injection of vascular endothelial growth factor gene".

Safi et al., J Mol Cell Dardiol, 1997, "Gene theraphy with angiogenic factors: a new potential approach to the treatment of ischemic diseases".

Asahara et al., Z kardiol, 1997, "Arterial gene therapy: a molecular biological perspective for the treatment of arterial ischemia".

Tsurumi et al., Circulation, 1996, "Direct intramuscular gene transfer of naked DNA encoding vascular endothelial growth factor augments collateral development and tissue perfusion".

Takeshita et al., Lab Invest, 1996, "Gene transfer of naked NDA encoding for three isoforms of vascular endothelial growth factor stimulates collateral development in vivo".

Majesky, Circulation, 1996, "A little VEGF goes a long way. Therapeutic angiogenesis by direct injection of vascular endothelial growth factor–encoding plasmid DNA".

Darius et al, Herz, 1997, "Locating drug deliver and gene therapy".

Tuder et al., "Role of vascular endothelial growth factor in hypoxia and monocrotaline induced pulmonary hypertension".

* cited by examiner

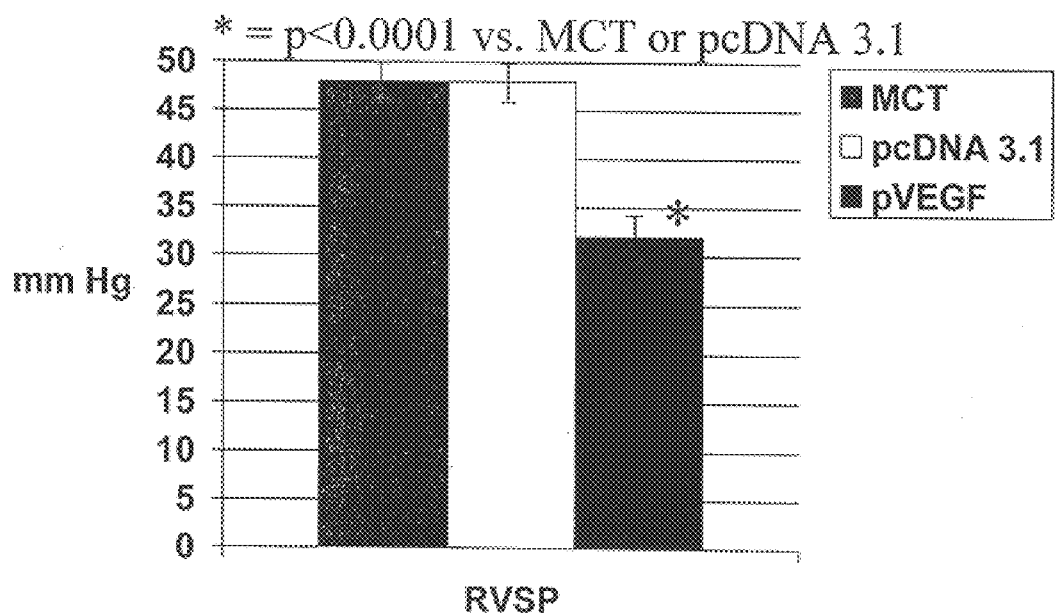
Figure 3: RVSP following MCT and Gene Transfer (Prevention)

Figure 4: RV/LV ratio following MCT and Gene Transfer (Prevention)
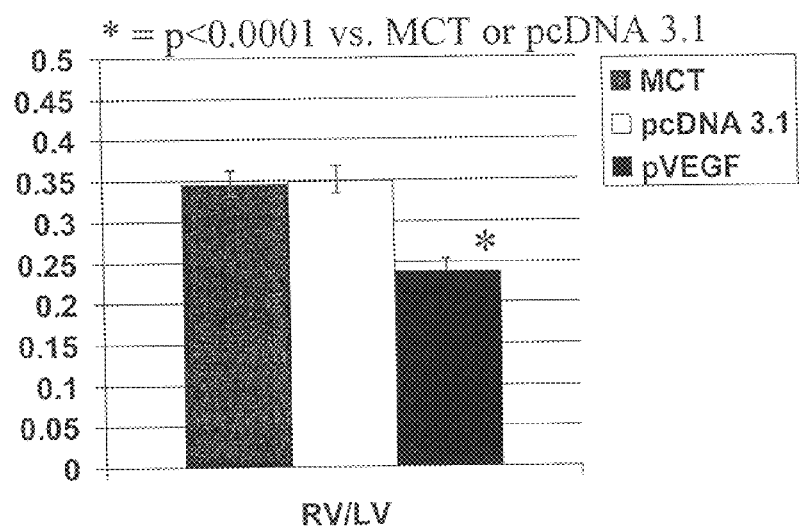

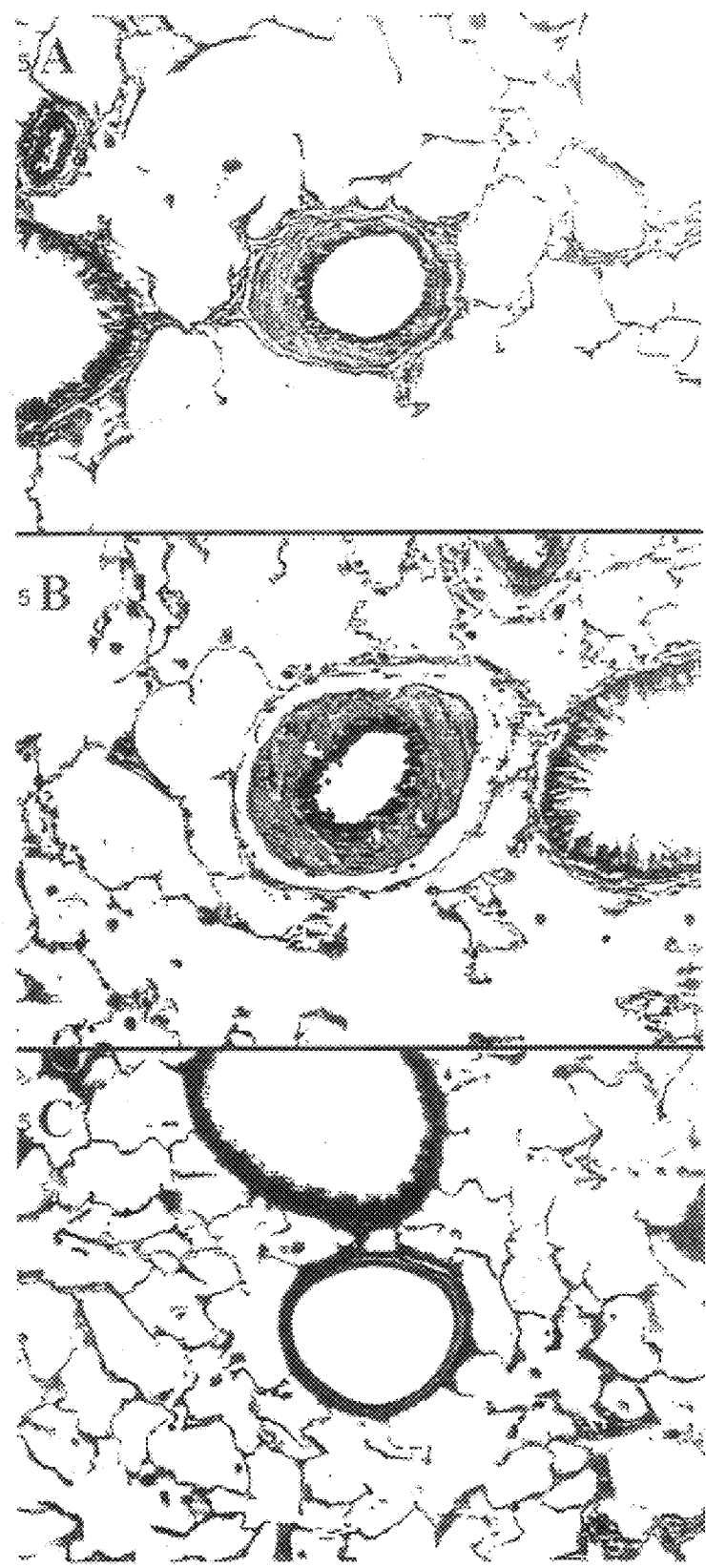

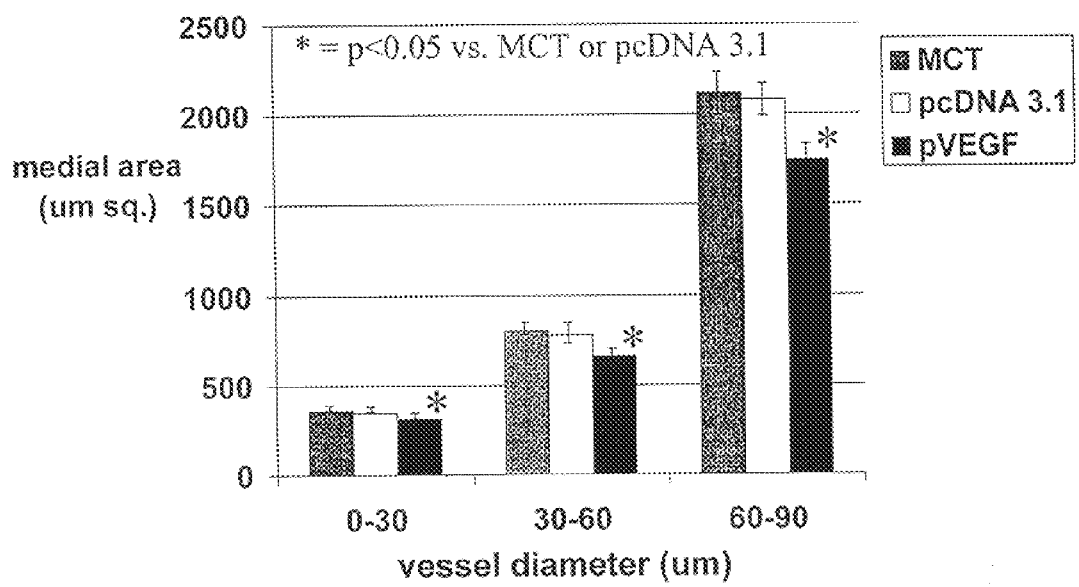

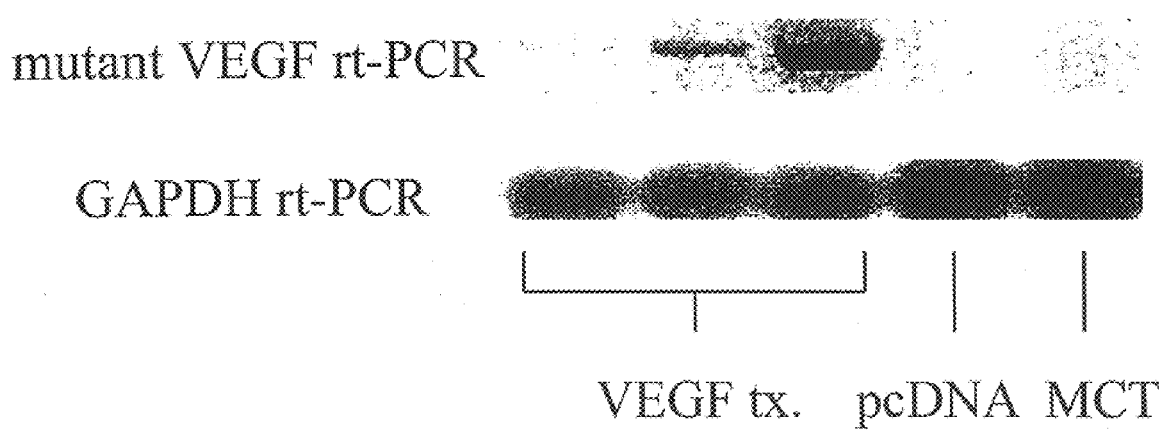

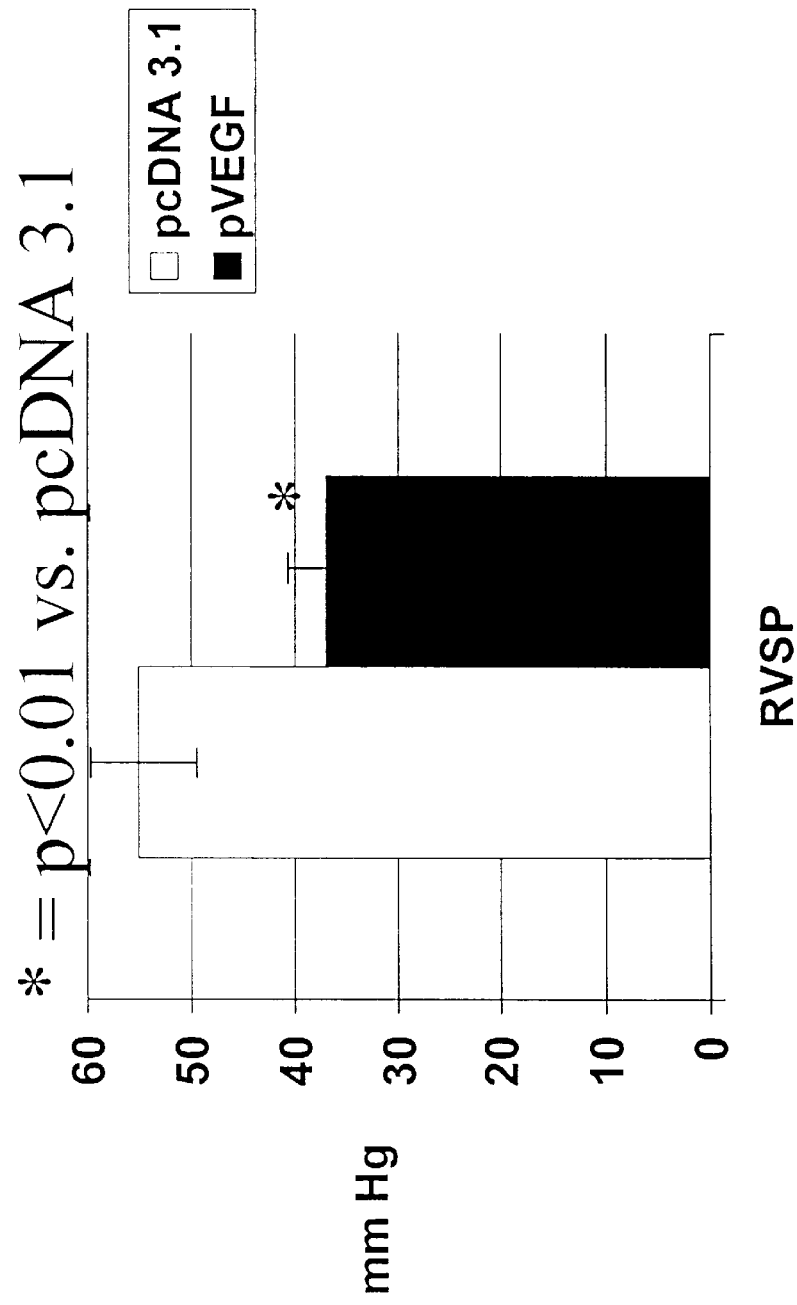
Figure 8: RVSP following MCT and Gene Transfer (Reversal)

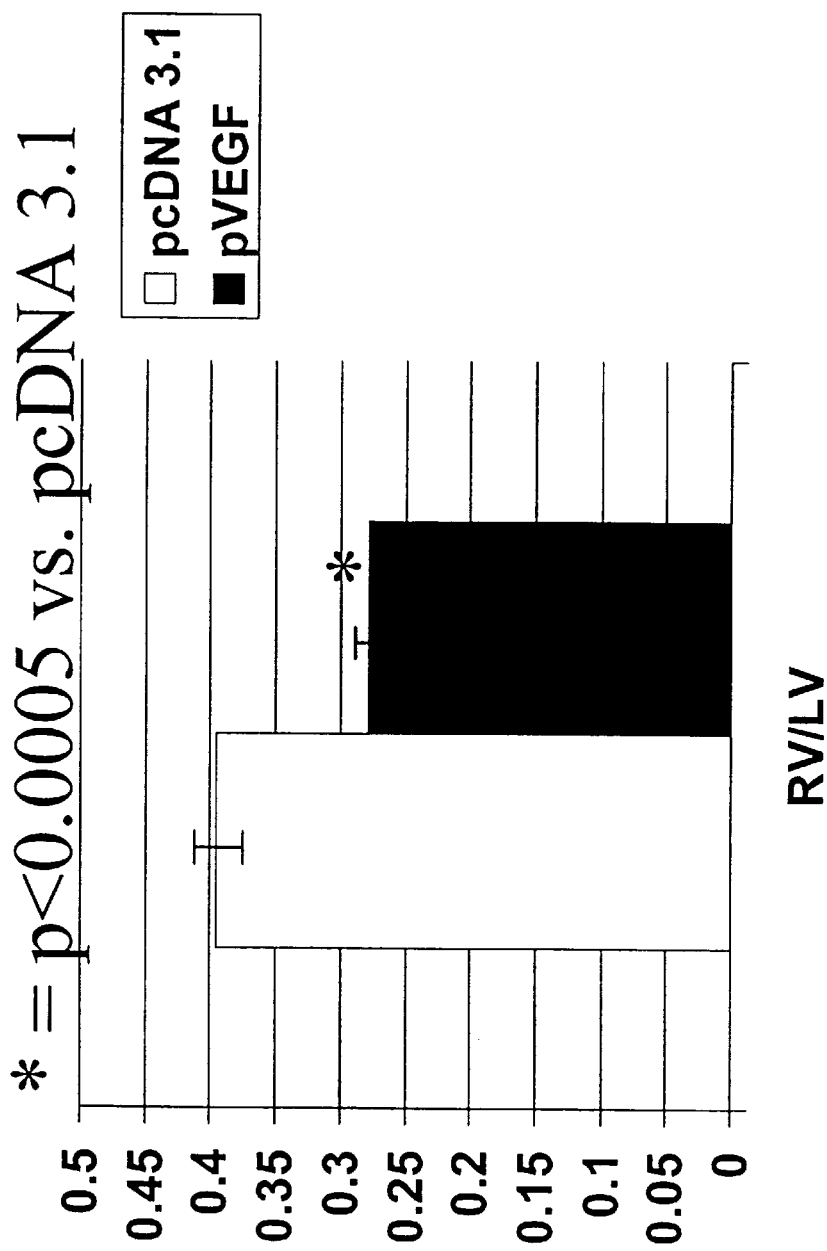
Figure 9: RV/LV ratio following MCT and Gene Transfer (Reversal)

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 1
tcgggcctcc gaaaccatga                                                  20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 2
cctggtgaga gatctggttc                                                  20

<210> SEQ ID NO 3
<211> LENGTH: 33
<212> TYPE: DNA

```
<213> ORGANISM: Artificial Sequence
<220> FEATURE:
<223> OTHER INFORMATION: Description of Artificial Sequence:Primer

<400> SEQUENCE: 3
cgctactggc ttatcgaaat taatacgact cac                               33

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence:Primer

<400> SEQUENCE: 4
ggccttggtg aggtttgatc cgcataat                                     28

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:Primer

<400> SEQUENCE: 5
ctctaaggct gtgggcaagg tcat                                         24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence:Primer

<400> SEQUENCE: 6
gagatccacc accctgttgc tgta                                         24

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 7
tcgggcctcc gaaaccatga                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:Primer

<400> SEQUENCE: 8
cctggtgaga gatctggttc                                              20
```

CELL-BASED GENE THERAPY FOR THE PULMONARY SYSTEM

CROSS-REFERENCE TO RELATED APPLICATION

This application is a continuation-in-part of U.S. patent application Ser. No. 09/276,654 filed Mar. 26, 1999 and currently pending, awaiting examination. The entire disclosure of that application is incorporated herein by reference.

FIELD OF THE INVENTION

This invention relates to medical treatments and composition and procedures useful therein. More specifically, it relates to cell-based gene transfer systems for administration to the pulmonary system of a mammalian patient.

BACKGROUND OF THE INVENTION

Cell-based gene transfer is a known, albeit relatively new and experimental, technique for conducting gene therapy on a patient. In this procedure, DNA sequences containing the genes which it is desired to introduce into the patient's body (the trans-genes) are prepared extracellularly, e.g. by using enzymatic cleavage and subsequent recombination of DNA with insert DNA sequences. Mammalian cells such as the patient's own cells are then cultured in vitro and treated so as to take up the transgene in an expressible form. The trans-genes may be foreign to the mammalian cell, additional copies of genes already present in the cell, to increase the amount of expression product of the gene or copies of normal genes which may be defective or missing in a particular patient. Then the cells containing the trans-gene are introduced into the patient, so that the gene may express the required gene products in the body, for therapeutic purposes. The take-up of the foreign gene by the cells in culture may be accomplished by genetic engineering techniques, e.g. by causing transfection of the cells with a virus containing the DNA of the gene to be transferred by lipofection, by electro-poration, or by other accepted means to obtain transfected cells, [such as the use of viral vectors]. This is sometimes followed by selective culturing of the cells which have successfully taken up the transgene in an expressible form, so that administration of the cells to the patient can be limited to the transfected cells expressing the trans-gene. In other cases, all of the cells subject to the take-up process are administered.

This procedure has in the past required administration of the cells containing the trans-gene directly to the body organ requiring treatment with the expression product of the trans-gene. Thus, transfected cells in an appropriate medium have been directly injected into the liver or into the muscle requiring the treatment, or via the systemic arterial circulation to enter the organ requiring treatment.

Previous attempts to introduce such genetically modified cells into the systemic arterial circulation of a patient have encountered a number of problems. For example, there is difficulty in ensuring a sufficiently high assimilation of the genetically modified cells by the specific organ or body part where the gene expression product is required for best therapeutic benefit. This lack of specificity leads to the administration of excessive amounts of the genetically modified cells, which is not only wasteful and expensive, but also increases risks of side effects. In addition, many of the transplanted genetically modified cells do not survive when administered to the systemic arterial circulation, since they encounter relatively high arterial pressures. Infusion of particulate materials, including cells, to other systemic circulations such as the brain and the heart, may lead to adverse consequences due to embolization, i.e. ischemia and even infarction.

It is an object of the present invention to provide a novel procedure of cell based gene transfer to mammals.

It is a further and more specific object of the invention to provide novel procedures of cell-based gene therapy utilizing dermal (or other) fibroblast cells.

It is a further object of the invention to provide novel genetically engineered cells containing trans-genes expressing angiogenic factors.

It is a further and more specific object of the invention to provide novel uses and novel means of administration of angiogenic factors in human patients.

SUMMARY OF THE INVENTION

The present invention is based upon the discovery that the pulmonary system of a mammal, including a human, offers a potentially attractive means of introducing genetically altered cells into the body, for purposes of gene therapy, i.e. cell based gene transfer. The pulmonary system has a number of unique features rendering it particularly suited to a cell-based gene transfer. Thus, low arterial pressure and high surface area with relatively low shear in the microcirculation of the lungs increase the chances of survival of the transplanted cells. High oxygenation in the microcirculation of the ventilated lung also improves the viability of the transplanted cells.

Moreover, the pulmonary circulation functions as a natural filter, and is able to retain the infused cells efficiently and effectively. Also, the lung has a dual circulation (pulmonary arterial and bronchial). This is in contra-distinction to other systemic circulations, such as the brain and the heart, where the infusion of particulate materials such as cells could lead to the aforementioned adverse consequences. The lung presents a massive vascular system. The high surface area of the pulmonary endothelium allows the migration of the transplanted cells trapped in the micro-circulation across the endothelial layer to take up residence within the perivascular space.

The pulmonary circulation, unlike any other circulation in the body, receives the entire output of the heart. Accordingly, it offers the greatest opportunity to release a gene product into the circulation. This distinct property of the lung is particularly useful for pulmonary gene therapy and for the treatment of a systemic disorders, as well as a pulmonary disorder.

It is believed that the transfected cells become lodged in the small artery-capillary transition regions of the pulmonary circulation system, following simple intravenous injection of the transfected cells to the patient. Products administered intravenously move with the venous circulation to the right side of the heart and then to the lungs. The transfected cells administered according to the invention appear to lodge in the small arteriolar-capillary transition regions of the circulatory system of the lungs, and then transmigrate from the intraluminal to the perivascular space, from where they deliver expression products of the trans-genes to the lungs, making the process to the present invention especially applicable to treatment of pulmonary disorders. Some factors, especially stable factors can be secreted to the general circulation for treatment of disorders of other body organs.

Thus, according to a first aspect of the present invention, there is provided a process of conducting gene therapy in a mammalian patient, which comprises administering to the pulmonary system of the patient, genetically modified mammalian cells containing at least one expressible trans-gene which is capable of producing at least one gene product in the pulmonary circulation after administration thereto.

According to another, more specific aspect of the invention, there are provided genetically modified mammalian cells selected from fibroblasts, endothelial cells and progenitor cells, said cells containing at least one expressible trans-gene coding for a therapeutic factor.

A further aspect of the present invention provides the use in the preparation of a medicament for administration to a mammalian patient to alleviate symptoms of a disorder, of viable, transfected mammalian cells containing at least one expressible trans-gene coding for a therapeutic factor.

Yet another aspect of the present invention is a process of preparing genetic modifications of mammalian cells selected from fibroblasts, endothelial cells and progenitor cells, which comprises transfecting said mammalian cells with at least one gene coding for a therapeutic factor, to produce transfected cells capable of expressing said therapeutic factor in vivo.

An additional aspect of the present invention is the treatment of pulmonary hypertension (PH). Primary pulmonary hypertension (PPH) and other causes of PH are associated with severe abnormalities in endothelial function, which likely play a critical role in its pathogenesis. The vasodilatory, anti-thrombotic and anti-proliferative factor, nitric oxide (NO) has been demonstrated to decrease pulmonary pressures in both experimental and clinical situations. However, long-term viral-based methods may cause significant local inflammation. Other, previous attempts to treat PPH have involved the use of prostacyclin, using continuous administration, but this is a difficult and expensive procedure, liable to give rise to side effects.

The present invention provides, from this additional aspect, a method of alleviating the symptoms of PPH (and other causes of PH) which comprises administering to the pulmonary system of a patient suffering therefrom, at least one angiogenic factor, or a precursor or genetic product capable of producing and releasing into the pulmonary circulation at least one angiogenic factor.

An embodiment of this additional aspect of the present invention is the delivery to a patient suffering from PPH of genetically modified cells containing a gene capable of expressing in vivo at least one angiogenic factor, by a process of cell-based gene transfer as described above. This additional aspect of invention, however, is not limited to any specific form of administration, but pertains generally to the use of angiogenic factors and precursors thereof which produce angiogenic factors in situ, in treating or alleviating the symptoms of PPH, delivered to the pulmonary circulation by any suitable means.

DESCRIPTION OF THE PREFERRED EMBODIMENTS

A wide variety of trans-genes encoding therapeutic factors can be used in the processes and products of the present invention. While treatment of pulmonary system disorders is a primary focus of the invention, it is not limited to such treatments. Therapeutic factors expressed by the trans-genes and delivered by the circulation of other body organs downstream of the lungs are within the scope of this invention. Trans-genes expressing therapeuticfactors such as Factor VIII for treatment of classical haemophelia, and other clotting factors for treating various bleeding disorders may be used. Other examples include:

trans-genes expressing hormones, for example growth hormone for treatment of hypopituitary dysfunction, insulin, (thyroid stimulating hormone (TSH) for treatment hypothyroidism following pituitary failure, and other hormones;

trans-genes expressing beneficial lipoproteins such as Apo 1 and other proteins/enzymes participating in lipid metabolism such as lipoprotein lipase;

trans-genes expressing prostacyclin and other vasoactive substances;

trans-genes expressing anti-oxidants and free radical scavengers;

trans-genes expressing soluble cytokine receptors to neutralize actions of damaging levels of immune mediators, for example soluble TNFα receptor, or cytokine receptor antagonists, for example IL1ra;

trans-genes expressing soluble adhesion molecules, for example ICAM-1, to interrupt pathological cell adhesion processes such as those which occur in inflammatory diseases;

trans-genes expressing soluble receptors for viruses to inhibit infection of cells, e.g. CD4, CXCR4, CCR5 for HIV;

trans-genes expressing cytokines, for example IL-2, to activate immune responses for combatting infections;

the cystic fibrosis gene, as a trans-gene.

The transfected cells lodged in the lung and containing trans-genes expressing such factors and other products will act as a systemic source of the appropriate factor.

One preferred aspect of the present invention is the treatment of pulmonary hypertension (PH). Primary pulmonary hypertension (PPH) and other causes of PH are associated with severe abnormalities in endothelial function, which likely play a critical role in its pathogenesis. The vasodilatory, anti-hrombotic and anti-proliferative factor, nitric oxide (NO) has been demonstrated to decrease pulmonary pressures in both experimental and clinical situations. However, long-term viral-based methods may cause significant local inflammation. Other, previous attempts to treat PPH have involved the use of prostacyclin, using continuous administration, but this is a difficult and expensive procedure, liable to give rise to side effects.

The present invention provides, from this second preferred aspect, a method of alleviating the symptoms of PPH (and other causes of PH) which comprises administering to the pulmonary system of a patient suffering therefrom transformed mammalian fibroblast cells from dermal or other origins, endothelial cells or progenitor cells derived from bone marrow or isolated from the systemic circulation, said transfected cells including at least one expressible trans-gene coding for an angiogenic factor for release thereof into the pulmonary circulation.

Specific examples of useful angiogenic factors for delivery by way of trans-genes in cells, or by way of other routes of the additional aspect of this invention include nitric oxide synthase (NOS); vascular endothelial growth factor (VEGF) in all of its various known forms, i.e. VEGF$_{165}$ which is the commonest and is preferred for use herein, VEGF$_{205}$, VEGF, $_{189}$, VEGF$_{121}$, VEGF$_B$ and VEGF$_C$(collectively referred to herein as VEGF); fibroblast growth factor (FGF, acid and basic), angiopoietin-1 and other angiopoietins, transforming growth factor-β (TGF-β), and hepatic growth factor (scatter factor) and hypoxia inducible factor (HIF). DNA sequences constituting the genes for these angiogenic factors are known, and they can be prepared by the standard methods of recombinant DNA technologies (for example enzymatic cleavage and recombination of DNA), and introduced into mammalian cells, in expressible form, by standard genetic engineering techniques such as those mentioned above (viral transfection, electroporation, lipofection, use of polycationic proteins, etc). VEGF is the preferred angiogenic factor, on account of the greater experience with this factor and its level of effective expression in practice.

In the additional aspect of the invention, the angiogenic factors can be administered directly to the patient, e.g. by direct infusion of the angiogenic factor, into the vasculature intravenously. They can also be administered to the patient by processes of inhalation, whereby a replication-deficient recombinant virus coding for the angiogenic factor is introduced into the patient by inhalation in aerosol form, or by intravenous injection of the DNA constituting the gene for the angiogenic factor itself (although this is inefficient). Administration methods as used in known treatments of cystic fibrosis can be adopted.

Angiogenic factors such as those mentioned above have previously been proposed for use as therapeutic substances in treatment of vascular disease. It is not to be predicted from this work, however, that such angiogenic factors would also be useful in treatment of pulmonary hypertension. Whilst it is not intended that the scope of the present invention should be limited to any particular theory or mode of operation, it appears that angiogenic growth factors may also have properties in addition to their ability to induce new blood vessel formation. These other properties apparently include the ability to increase nitric oxide production and activity, and/or decrease the production of endothelin-1, in the pulmonary circulation, so as to improve the balance of pulmonary cell nitric oxide in endothelin-1 production.

In preparing cells for transfection and subsequent introduction into a patient's pulmonary system, it is preferred to start with somatic mammalian cells obtained from the eventual recipient of the cell-based gene transfer treatment of then present invention. A wide variety of different cell types may be used, including fibroblasts, endothelial cells, smooth muscle cells, progenitor cells (e.g. from bone marrow or peripheral blood), adicytes and others. Dermal fibroblasts are simply and readily obtained from the patient's exterior skin layers, readied for in vitro culturing by standard techniques. Endothelial cells are harvested from the eventual recipient, e.g. by removal of a saphenous vein and culture of the endothelial cells. Progenitor cells can be obtained from bone marrow biopsies or isolated from the circulating blood, and cultured in vitro. The culture methods are standard culture techniques with special precautions for culturing of human cells with the intent of re-implantation.

It is strongly preferred, in accordance with the present invention, to use dermal fibroblasts from the patient, as the cells for gene transfer. Given the fact that the logical choice of cell types for one skilled in the art to make would be a cell type naturally found in the patient's pulmonary system, such as smooth muscle cells, the use of fibroblasts is counter-intuitive. Surprisingly, it has been found that fibroblasts are eminently suitable for this work, exhibiting significant and unexpected advantages over cells such as smooth muscle cells. They turn out to be easier to grow in culture, and easier to transfect with a trans-gene, given the appropriate selection of technique. They yield a higher proportion of transfectants, and a higher degree of expression of the angiogenic factors in vivo, after introduction into the patient's pulmonary system. The anticipated greater risk with fibroblasts of possibly causing fibrosis in the pulmonary system, as compared with smooth muscle cells, has not materialized.

The somatic gene transfer in vitro to the recipient cells, i.e. the genetic engineering, is performed by standard and commercially available approaches to achieve gene transfer, as outlined above. Preferably, the method includes the use of poly cationic proteins (e.g. SUPERFECT*) or lipofection (e.g. by use of GENEFECTOR), agents available commercially and which enhance gene transfer. However, other methods besides lipofection and polycationic protein use, such as, electroporation, viral methods of gene transfer including adeno and retro viruses, may be employed. These methods and techniques are well known to those skilled in the art, and are readily adapted for use in the process of the present invention. Lipofection is the most preferred technique, for use with dermal fibroblast host cells, whereas the use of polycationic proteins is preferred for use with smooth muscle cells.

The re-introduction of the genetically engineered cells into the pulmonary circulation can be accomplished by infusion of the cells either into a peripheral vein or a central vein, from where they move with the circulation to the pulmonary system as previously described, and become lodged in the smallest arteriols of the vascular bed of the lungs. Direct injection into the pulmonary circulation can also be adopted, although this is less convenient. The infusion can be done either in a bolus form i.e. injection of all the cells during a short period of time, or it may be accomplished by a continuous infusion of small numbers of cells over a long period of time, or alternatively by administration of limited size boluses on several occasions over a period of time.

While the transfected cells themselves are largely or completely retained in the pulmonary circulation, and especially in the arteriols of the patient's lungs, the expression products of the trans-genes thereof are not restricted in this manner. They can be expressed and secreted from the transfected cells, and travel through the normal circulation of the patient to other, downstream body organs where they can exert a therapeutic effect. Thus, while a preferred use of the process of the invention is in the treatment of pulmonary disorders, since the expression products initially contact the patient's pulmonary system, it is not limited to such treatments. The transfectants can contain trans-genes expressing products designed for treatment of other body organs of the patient. Such products expressed in the pulmonary system will target the other, predetermined organs and be delivered thereto by the natural circulation system of the patient.

The invention is further described for illustrative purposes, in the following specific, non-limiting Examples.

BRIEF DESCRIPTION OF THE DRAWINGS

The invention will now be described, by way of example only, with reference to the accompanying drawings, in which:

FIG. 3 provides a graphic representation of right ventricular systolic pressure four weeks after monocrotaline injection and cell-based gene transfer as described in Example 7;

FIG. 4 provides a graphic representation of right ventricular to left ventricular plus septal weight ratio four weeks after monocrotaline injection and cell-based gene transfer as described in Example 7;

FIG. 5A illustrates the smooth muscle hypertrophic and hyperplastic response observed in mid-sized pulmonary vessels four weeks following subcutaneous injection of monocrotaline as described in Example 7;

FIG. 5B shows similar results as FIG. 5A in animals transfected with the control vector, pcDNA 3.1 as described in Example 7;

FIG. 5C shows similar results as FIG. 5A following cell-based gene transfer of VEGF as described in Example 7;

FIG. 6 is a graphic representation of medial area following monocrotaline injection and gene transfer as described in Example 7;

FIG. 7 graphically represents results obtained by selectively amplifying the exogenous VEGF transcript as described in Example 7;

FIG. 8 provides a graphic representation of right ventricular systolic pressure following monocrotaline injection and delayed gene transfer as described in Example 8; and FIG. 9 provides a graphic representation of right ventricular to left ventricular plus septal weight ratio following monocrotaline injection and delayed gene transfer (reversal experiments) as described in Example 8.

EXAMPLE 1

Pulmonary Artery Explant Culture

Figure 1:
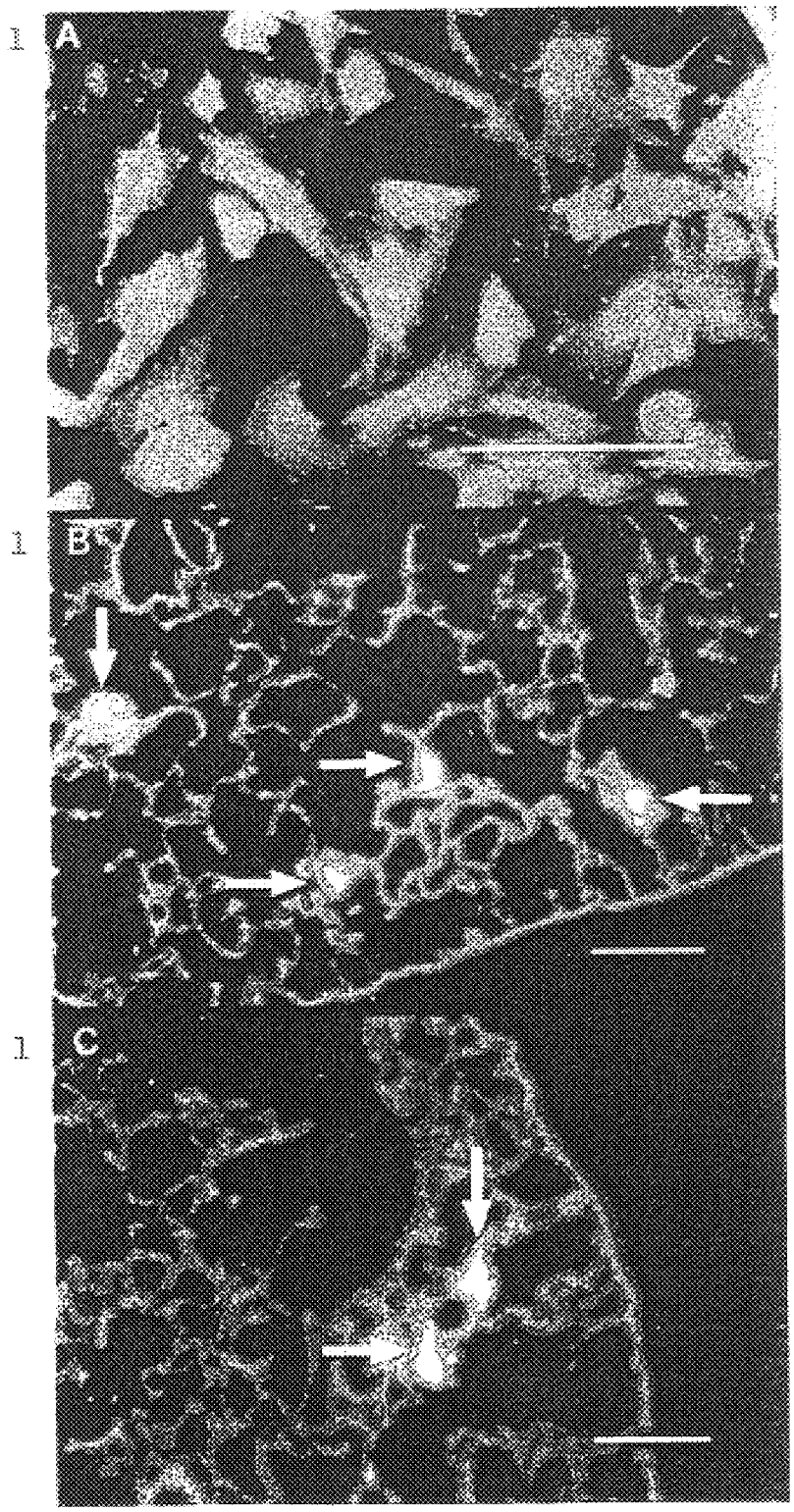
FIG. 1A illustrates fluorescence of pulmonary artery smooth muscle cells immediately following incubation with the viable fluorophore CMTMR, as described below in Example 2.
FIGS. 1B and 1C respectively illustrate multiple cell-shaped fluorescent signals at fifteen minutes and 48 hours after jugular injection as described in Example 5.

Fisher 344 rats (Charles River Co.) were obtained at 21 days of age and were sacrificed by overdose with ketamine and xylazine. The main pulmonary artery was excised and transferred immediately into a phosphate-buffered saline (PBS) solution containing 2% penicillamine and streptomycin (Gibco BRL, Burlington, Ontario). The adventitia was carefully removed with sterile forceps, the artery opened longitudinally and the endothelium removed by abrasion of the intimal surface with a scalpel. The vessel was cut into approximately 4 millimeter square pieces which were placed intimal surface down on individual fibronectin-coated (Sigma Chemical Co., Mississauga, Ontario) tissue culture plates (Falcon, Becton Dickinson Canada, Mississauga, Ontario). The explants were then grown in Dulbecco's Modified Eagle Media with 10% fetal calf serum (FCS) and 2% penicillamine and streptomycin (all Gibco BRL), in a humidified environment with 95% $O_2$ and 5% $CO_2$ at 37° C., with the media being changed every second day. Explants were passaged using 0.05% trypsin/EDTA (Gibco BRL) once many cells of a thin, fusiform smooth muscle cell phenotype could be clearly seen growing from the pulmonary artery segment, at which time the remaining explanted tissue was removed. The cells were then grown in DMEM with 10% FCS and 2% penicillamine and streptomycin until they were to be used in further experiments.

EXAMPLE 2

Alpha-Actin and Von Willebrand Factor Fluorescent Staining

To confirm their smooth muscle cell identity and rule out endothelial cell contamination, cells at the third passage were plated onto cover slips and grown until 70% confluent, at which time they were fixed in acetone at room temperature for 10 minutes. The cells were incubated with FCS for 30 minutes at 37° C. to block non-specific bonding sites, and then with a monoclonal anti-alpha-actin antibody (5 micrograms/millilitre) (Boehringer Mannheim) and a rabbit-derived polyclonal anti-von Willebrand Factor antibody (1:200 dilution) (Sigma) for 60 minutes at 37° C. in a covered humidified chamber. Negative control cover slips were incubated with PBS for the same duration of time. The cover slips were then washed in PBS, and incubated for 60 minutes at room temperature in a PBS solution containing a Cy3-conjugated donkey anti-mouse IgG antibody (1:200 dilution) (Jackson ImmunoResearch Laboratories), a fluorescein isothiocyanate (FITC)-conjugated goat anti-rabbit IgG antibody (1:200) (Jackson ImmunoResearch Laboratories), and Hoescht 33258 (Sigma), a fluorescent nuclear counterstain. The cover slips were again washed with PBS, and mounted using a 1:1 solution of PBS and gycerol. Slides were examined using an Olympus BX50 epifluorescent microscope with standard fluorescein, rhodamine and auto-fluorescent emission and excitation filters. For each cover slip the immunofluorescence for action, vWF, and for the nuclear counterstain Hoescht was indicated as positive or negative.

All of the explant derived cultures were found to be at least 97% pure smooth muscle cell with very rare endothelial contamination. This could be attributed to the vigorous debridement of the endothelial lining during the initiation of the explant, and early passaging with removal of the residual explant material.

Fluorescent Cell Labeling—Cells between the fifth and ninth passages were grown until 80% confluent and were then labeled with the viable fluorophore, chloromethyl trimethyl rhodamine (CMTMR, Molecular Probes Inc., Eugene, Oreg.). CMTMR affords a very accurate method of detecting ex vivi labeled cells, as the molecule undergoes irreversible esterification and glucoronidation after passing into the cytoplasm of a cell and thereby generates a membrane-impermeable final product. This active fluorophore is then unable to diffuse from the original labeled cell into adjacent cells or structures, and may be detected in vivo for several months, according to the manufacturer. The fluorescent probe was prepared by dissolving the lyophilized product in dimethyl sulfoxide (DMSO) to a concentration of 10 millimolar. This solution was stored at −20° C., an diluted to a final concentration of 25 micromolar in serum-free DMEM immediately prior to use. Cells were exposed to the labeling agent for 45 minutes, and were then washed with PBS twice and the regular media (DMEM with 10% FCS and 2% penicillin and streptomycin) replaced. The cells were grown overnight and harvested 24 hours later for injection into the internal jugular vein of recipient Fisher 344 rats.

A series of in vitro experiments was also performed by plating the cells on cover slips and the incubating them with the fluorophore to determine the quality and duration of fluorescence over time. Immediately after incubation with the fluorophore, CMTMR, at a concentration of 25 micromolar, 100% of cultured cells were found to fluoresce intensely when examined under a rhodamine filter (FIG. 1A). The white scale bar in FIG. 1A is 50 microns in length. Cells were also examined 48 hours and 7 days after labeling, and despite numerous cell divisions 100% of the cells present on the cover slip continued to fluoresce brightly (data not shown).

EXAMPLE 3

Ex Vivo Cell Transfeccion with the CMV-βGal Plasmid

The vector CMV-βGal (Clontech Inc., Palo Alto, Calif.), which contains the beta-galactosidase gene under the control of the cytomegalovirus enhancer/promoter sequence, was used as a reporter gene to follow the course of in vivo transgene expression. The full-length coding sequence of $VEGF_{165}$ was generated by performing a reverse transcription polymerase chain reaction using total RNA extracted from human aortic smooth muscle cells and the following sequence specific primers: sense 5' TCGGGCCTC-CGAAACCATGA 3' (SEQ ID. No.1)antisense 5' CCTGGT-GAGAGATCTGGTTC 3' (SEQ ID. No.2). This generated a 649 bp fragment which was cloned into the pGEM-T vector (Promega, Madison, Wis.), and sequenced to confirm identity. The fragment was then cloned into the expression vector pcDNA 3.1 at the EcoR1 restriction site, and correct orientation determined using a differential digest. The insert deficient vector (pcDNA 3.1) was used as a control for the monocrotaline experiments. All plasmid DNA was introduced into a JM109 strain of E. Coli via the heat-shock method of transformation, and bacteria was cultured overnight in LB media containing 100 micrograms/millilitre of ampicillin. The plasmid was then purified using an endotoxin-free purification kit according to the manufacturer's instructions (Qiagen Endotoxin-Free Maxi Kit, Qiagen Inc., Mississauga, Ontario), producing plasmid DNA with an $A_{260}/A_{280}$ ratio of greater than 1.75, and a concentration of at least 1.0 micrograms/microliter. Smooth muscle cells between the fifth and ninth passages were transfected using Superfect (Qiagen Inc., Mississauga, Ontario). This method was used to avoid the use of viral vectors and simultaneously obtain significant in vitro transfection efficiencies. The Superfect product is composed of charged polycations around which the plasmid DNA coils in a manner similar to histone-genomic DNA interactions. This Superfect-DNA complex then interacts with cell surface receptors and is actively transported into the cytoplasm, after which the plasmid DNA can translocate to the nucleus. This technique allows the transfection reaction to be performed in the presence of serum (an important consideration in sensitive primary cell lines), and produces no toxic metabolites.

Cells between the fifth and ninth passages were trypsinized the day prior to transfection to obtain a density of $5\times10^5$ cells/dish. The following day, 5 micrograms of plasmid DNA was mixed with 300 microlitres of serum-free DMEM in a sterile microcentrifuge tube. The plasmid-media solution was then vortexed with 50 microlitres of Superfect transfection agent (Qiagen), after which the tubes were incubated for 10 minutes at room temperature. The transfection mixture was then combined with 3 milliliters of DMEM with 10% FCS and 2% penicillin and streptomycin and applied to the culture dishes after the cells had been washed with PBS. The solution was allowed to incubate at 37° C. for 4 hours, and the cells were then washed with PBS twice and the standard media replaced. The transfected cells were allowed to grow overnight and were then harvested 24 hours later for animal injection. For every series of transfection reactions that were performed, one 100 millimeter dish of pulmonary artery smooth muscle cells was stained in vitro, to provide an estimate of the transfection efficiency of the total series.

In a total of 15 separate transfection reactions using the pCMV-βGal plasmid, an average transfection efficiency of 11.4% was obtained with the primary pulmonary artery smooth muscle cells. No staining was seen in mock transfected cultures.

EXAMPLE 4

Animal Surgery

All animal procedures were approved by the Animal Care Committee of St. Michael's Hospital, Toronto, Canada. Six week old Fisher 344 rats (Charles River Co., St. Constant, Quebec) were anesthetized by intraperitoneal injection of xylazine (4.6 milligrams/kilogram) and ketamine (70 milligrams/kilogram), and the cervical area shaved and cleaned with iodine and ethanol. A midcervical incision was made with a scalpel and the right internal, external and common jugular veins identified. Plastic tubing of 0.02 millimetres external diameter was connected to a 23 gauge needle and flushed with sterile saline (Baxter). Thus tubing was then used to cannulate the external jugular vein and was introduced approximately 5 centimetres into the vein to what was estimated to be the superior vena caval level, and rapid venous blood return was used to confirm the catheter location.

For experiments to determine the time course of cell survival and transgene expression in the lung, pulmonary artery smooth muscle cells which had been labeled with the fluorophore CMTMR, or transfected with the plasmid vector CMV-βGal, were trypsinized, and centrifuged at 850 rpm for 5 minutes. The excise media was removed and the pellet of cells was resuspended in a total volume of 2 millilitres of phosphate-buffered saline (PBS). A 50 microlitre aliquot of these resuspended cells was then taken and counted on a hemocytometer grid to determine the total number of cells present per millilitre of PBS. The solution was then divided into 1 millilitre aliquots of approximately 500,000 cells and transferred in a sterile manner to the animal care facility. These cells were then resuspended by gentle vortexing and injected into the animals via the external jugular vein catheter. The solution was infused slowly over one to two minutes and the catheter was then flushed again with sterile saline prior to removal. The external jugular vein was ligated, the incision closed with 3-0 interrupted absorbable sutures, and the animals allowed to recover from surgery.

EXAMPLE 5

Detection of Fluorescently-Labeled Cells in Tissue

At 15 minutes, 48 hours, 7 days, or 14 days after delivery of labeled cells (n=5 for each time-point except for 15 minutes where n=4), or saline injection (negative control, n=6), the animals were sacrificed by anesthetic overdose, and the chest cavity was opened. The pulmonary artery and trachea were flushed with saline, and the right and left lungs excised. Transverse slices were taken from the basal, medial and apical segments of both lungs, and specimens obtained from the liver, spleen, kidney and gastroenemius muscle. Tissue specimens were embedded i n OCT compound (Sakura Finetek U.S.A. Inc., Torrance, Calif.) en face, and then flash frozen in liquid nitrogen. Ten micron sections were cut from these frozen blocks at 2 different tissue levels separated by at least 200 microns, and these section s were then examined under a fluorescent microscope using a rhodamine filter, and the number of intensely fluorescing cells was counted in each en face tissue specimen.

To provide an estimate of the total number of labeled cells present within the entire lung, the total number of fluorescent cells were counted in each lung section and averaged over the number of sections counted. A mathematical approximation could be made of the total number of cells present within the lung by utilizing Simpson's rule for the volume of a truncated cone. This equation bases the total volume of a cone on the relative areas of 3 different sections such that:

$$\text{volume}=[(\text{area}^{basal\ section}+\text{area}^{middle\ section})\times\text{height of the lung}]/3+ [\text{area}^{apical\ section}/2\times\text{height of the lung}/3]+[\lambda/6\times(\text{height of the lung}/3)^3].$$

The height of the lung was measured after organ harvesting, and the area of each transverse section was determined by planimetry. The average number of cells present in the three sections, divided by the total volume of these sections yielded an estimate of the cell number per unit volume. By multiplying this number by the total lung volume an estimate of the total number of cells within the lung could be obtained. To correct for the appearance of a single cell in multiple adjacent lung sections, rats were injected with 500,000 CMTMR labeled cells and sacrificed acutely. The lungs were prepared, harvested and embedded in the usual manner, and twenty serial sections, each 5 microns in thickness, were taken through the lung parenchyma. Each section was examined using a rhodamine filter and distinct individual cells were identified and their presence determined on adjacent sections. The number of 5 micron sections in which a single cell could be identified was counted and the average dimensions of a pulmonary artery smooth muscle cell in vivo was obtained. The average diameter observed was 16.4±1.22 microns. Therefore, the total number of cells calculated using the Simpson's formula was multiplied by 0.61 to correct for the presence of 1 cell in, on average, each 1.64 ten micron sections.

Approximately 57±5% of the labeled cells could be identified within the lung 15 minutes after intravenous delivery, as shown by white arrows in FIG. 1B. Most of these cells appeared to be lodged in the capillary circulation at the alveolar level. By 48 hours after cell delivery, a significant decrease in the total number of fluorescent cells identified was noted (34±7%, $p<0.01$), and the location of the cells also appeared to have changed. Many bright fluorescent signals were now identified within the pulmonary parenchyma, or were lodged within the wall of small vascular structures as shown by the white arrows in FIG. 1C. The white scale bar in FIGS. 1B and 1C is 50 microns in length. At 7 and 14 days after injection, a further decrease in cell number was noted (16±3% and 15±5% respectively, both $p<0.001$ as compared to 15 minute time-point), however the cells appeared to remain in approximately the same location. No brightly fluorescent signals were seen in any of the lungs injected with non-labeled smooth muscle cells.

In the spleen, liver and skeletal muscle tissue no fluorescent signals were identified. In 2 out of 4 kidneys examined at 48 hours following injection, irregular fluorescent signals could be identified. None of these appeared to conform to the shape of a whole cell, and were presumed to represent those cells that were sheared or destroyed during cell injection or shortly thereafter. In addition, no fluorescent signals were identified in any organ outside of the lung 7 days after injection.

EXAMPLE 6

Detection of Beta-Galactosidase Expression in Tissue

At three time-points after cell-based gene transfer (48 hours, 7 days, and 14 days), animals (n=7 for each time-point) were sacrificed and the chest opened. The pulmonary artery was flushed with saline and the trachea was cannulated and flushed with 2% paraformaldehyde until the lungs were well inflated. Transverse slices were taken from the basal, medial and apical segments of both lungs, and specimens obtained from the liver, spleen, kidney and gastroenemius muscle of certain animals. The specimens were incubated in 2% paraformaldehyde with 0.2% glutaraldehyde for 1 hour, and then rinsed in PBS. The tissue was then incubated for 18 hours at 37° C. with a chromogen solution containing 0.2% 5-bromo4-chloro-3-indolyl-β-D-galactoside (X-Gal, Boehringer Mannheim, Laval, Quebec), 5 millimolar potassium ferrocyanide (Sigma), 5 millimolar potassium ferricyanide (Sigma), and 2 millimolar magnesium chloride (Sigma), all dissolved in phosphate buffered saline. The specimens were then rinsed in PBS, embedded in OCT compound (Miles Laboratories), cut into 10 micron sections, and counterstained with neutral red.

The en face sections were examined microscopically, and the number of intensely blue staining cells was determined. As one dish of cells was used for in vitro staining to determine the transfection efficiency for each reaction series, an estimate of the percentage of cells that were transfected with the reporter gene plasmid pCMV-βGal could be made for every animal. Using this information and the mathematical calculation described for approximating the number of fluorescent cells present, an estimate could be made of the total number of transfected cells remaining at the time of animal sacrifice.

Figure 2:
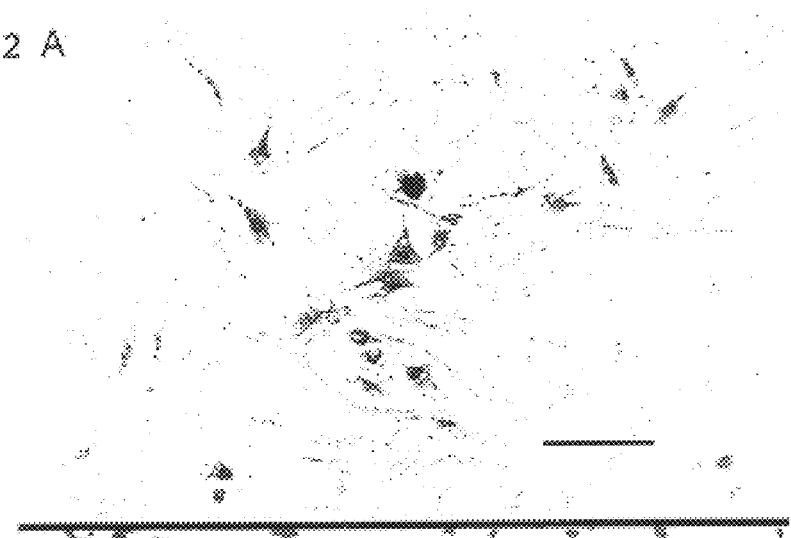
FIG. 2A shows that a transfection efficiency of about 15% could be obtained with the primary pulmonary artery smooth muscle cells in vitro, discussed in Example 6.
FIGS. 2B and 2C respectively show the staining in the lung at 48 hours and 14 days following injection, as described in Example 6.
Figure 2:
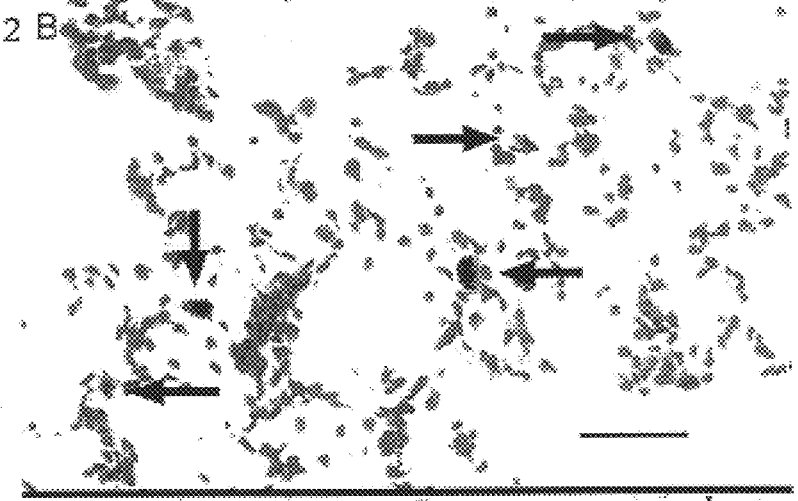
Figure 2:
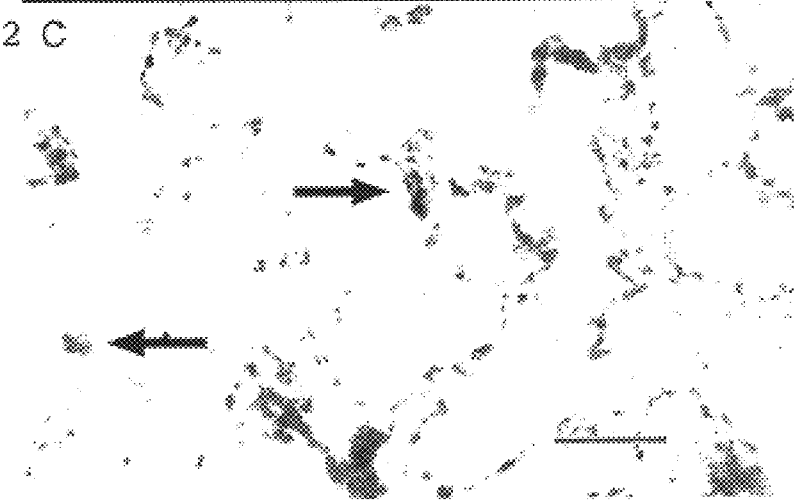

In a total of 15 separate transfection reactions using the pCMV-βGal plasmid, an average transfection efficiency of 13±0.5% was obtained with the primary pulmonary artery smooth muscle cells in vitro, and is 15% in FIG. 2A. No staining was seen in mock transfected cultures.

Following incubation with the X-Gal chromogen solution, microscopic evidence of cell-based transgene expression could be clearly seen at 48 hours after injection of pCMV-βGal transfected smooth muscle cells into the internal jugular vein (n=7), with multiple intense blue staining cells being seen throughout the lung (FIG. 2B), representing approximately 36±6% of the original transfected cells that were injected. As with the fluorescently-labeled cells, most of the beta-galactosidase expressing cells appeared to be lodged within the distal microvasculature. For example, in FIG. 2B, the staining cells are predominantly located in alveolar septae adjacent to small vessels, indicated by black arrows. By seven days after injection (n=4), a decline in the number of beta-galactosidase positive cells was noted (28±6%), and the intensity of staining also appeared to decrease. Again, the cells appeared to have either migrated into the pulmonary parenchyma or vascular wall. Fourteen days (n=6) after cell-based gene transfer, no further decrease in the number of cells identified was noted, but the intensity of beta-galactosidase staining of each cell had decreased further, as shown by the black arrows in FIG. 2C, which shows the remaining cells apparently located within the pulmonary parenchyma. The black scale bar in FIGS. 2A to 2C is 50 microns in length. No evidence of beta-galactosidase expression was detected in any of the lungs from animals (n=4, 3 at 7 days and 1 at 14 days) injected with non-transfected smooth muscle cells. At all three time-points, no evidence of pulmonary pathology, as determined by the presence of an abnormal polymorphonuclear or lymphocytic infiltrate, septal thickening or alveolar destruction, could be detected.

In the spleen and skeletal muscle of animals injected with transfected or non-transfected smooth muscle cells, no blue staining cells could be identified. Liver and renal specimens from animals injected with either transfected (n=5) or non-transfected (n=3) smooth muscle cells would occasionally show faint blue staining across the cut edge of the tissue (n=2 for each group), but no intense staining was seen at any time-point, and no staining was seen further than one high power field into the tissue.

EXAMPLE 7

Monocrotaline Prevention Studies

To determine if cell-based gene transfer of $VEGF_{165}$ would be capable of inhibiting the development of pulmonary hypertension in an animal model of disease, pulmonary artery smooth muscle cells which had been transfected with either pVEGF or pcDNA 3.1 were trypsinized and divided into aliquots of 500,000 cells.

Monocrotaline is a plant alkaloid, a metabolite of which damages the pulmonary endothelium, providing an animal model of pulmonary hypertension.

Six to eight week old Fisher 344 rats were then anesthetized and injected subcutaneously with either 80 milligrams/kilogram of monocrotaline (n=13) (Aldrich Chemical Co., Milwaukee, Wis.) alone, or with monocrotaline and, via a catheter in the external jugular vein, either 500,000 pVEGF (n=15), or pcDNA 3.1 (n=13) transfected cells. The vein was tied off, the incision closed in the normal fashion, and the animals allowed to recover. At 28 days after injection, animals were reanesthetized, and a Millar microtip catheter reinserted via the right internal jugular vein into the right ventricle. The right ventricular systolic pressure was recorded, and the catheter was then inserted into the ascending aorta and the systemic arterial pressure recorded. The animals were then sacrificed and the hearts excised. The right ventricular (RV) to left ventricular plus septal (LV) weight ratios (RV/LV ratio) were determined as an indicator of hypertrophic response to long-standing pulmonary hypertension. Lungs were flushed via the pulmonary artery with sterile phosphate-buffered saline, and were gently insufflated with 2% paraformaldehyde via the trachea. Pulmonary segments were then either snap frozen in liquid nitrogen for subsequent RNA extraction, or were fixed via immersion in 2% paraformaldehyde for paraffin embedding and sectioning. The right ventricular systolic pressures and RV/LV ratios were compared between the pVEGF, pcDNA 3.1, and monocrotaline alone groups.

RNA extracted from rat lungs was quantified, and 5 micrograms of total RNA from each animal was reverse transcribed using the murine moloney leukemia virus reverse-transcriptase, and an aliquot of the resulting cDNA was amplified with the polymerase chain reaction (PCR) using the following sequence-specific primers: sense 5≧ CGCTACTGGCTTATCGAAATTAAT ACGACTCAC 3' (SEQ ID. No.3), antisense 5' GGCCTTGGTGAG-GTTTGATCCGCATAAT 3' (SEQ ID. No.4), for 30 cycles with an annealing temperature of 65° C. Ten microlitres of a fifty microlitre reaction were run on a 1.5% agarose gel. The upstream primer was located within the T7 priming site of the pcDNA 3.1 vector and therefore should not anneal with any endogenous RNA transcript, and the downstream primer was located within exon 4 of the coding region of VEGF. Therefore, the successful PCR reaction would selectively amplify only exogenous VEGF RNA. To control for RNA quantity and quality, a second aliquot of the same reverse transcription reaction was amplified with the following primers for the constitutively-expressed gene GAPDH: sense 5' CTCTMGGCTGTGGGCMGGTCAT 3', antisense 5' GAGATCCACCACCCTGTTGCTGTA 3' (SEQ ID No.6). This reaction was carried out for 25 cycles with an annealing temperature of 58° C. Ten microlitres of a fifty microlitre reaction were run on a 1.5% agarose gel, and compared to the signal obtained from the VEGF PCR.

Paraformaldehyde fixed rat lungs were cut perpendicular to their long axis and were paraffin-embedded en face. Sections were obtained and stained using the elastin-von Giessen's (EVG) technique. The sections were assessed by a blinded observer who measured all vessels with a perceptible media within each cross-section under 40× magnification using the C+ computer imaging system. The medial area of each vessel was determined and an average was obtained for each vessel size from 0 to 30, 30 to 60, 60 to 90, 90 to 120, and greater than 120 microns in external diameter, for each animal. The averages from each size were compared between the pVEGF, pcDNA 3.1, and monocrotaline alone groups.

Four weeks following monocrotaline injection (n=11) alone, the right ventricular systolic pressure was increased to 48±2 mm Hg, and there was no improvement in those animals who received the pcDNA 3.1 transfected cells (n=10) with the average RVSP remaining at 48±2 mm Hg. However, in those animals treated with the pVEGF transfected cells (n=15) the RV pressure was significantly decreased to 32±2 mm Hg (p<0.0001). In this regard, see FIG. 3, which shows right ventricular systolic pressure (RVSP) graphed for the monocrotaline alone (MCT), the control vector transfected (pcDNA 3.1) and the animals injected with the VEGF transfected smooth muscle cells (pVEGF). Four weeks after injection of the pulmonary endothelial toxin monocrotaline and transfected cells, the RVSP was increased to 48 mm Hg in the MCT and pcDNA 3.1 groups, but was significantly decreased to 32 mm Hg in the pVEGF transfected animals.

As anticipated from the long-standing pulmonary hypertension, the RV/LV ratio was significantly elevated from baseline following monocrotaline injection (n=13) to 0.345±0.015 and was very similiar in the pcDNA 3.1 transfected group (n=13, 0.349±0.015, p>0.8). Following VEGF gene transfer (n=12) the ratio was significantly reduced to 0.238±0.012 (p<0.0001). No difference in aortic pressure was noted. See FIG. 4, in which the right ventricular to left ventricular plus septal weight ratio (RV/LV ratio) is used as a measure of long-standing pulmonary and right ventricular hypertension. Four weeks after injection of the pulmonary endothelial toxin monocrotaline and transfected cells, the RV/LV ratio is significantly elevated to 0.345 in the MCT group and 0.349 in the pcDNA 3.1 group, but was decreased to 0.238 in the pVEGF transfected animals.

Morphometric analysis of the tissue sections revealed that in both the monocrotaline alone and the pcDNA 3.1 treated groups, the medial area for the vessel groups from 0 to 30, 30 to 60 and 60 to 90 microns was significantly increased, as compared to the VEGF treated animals (p<0.05). In this regard, see FIGS. 5A to 5C showing that four weeks following subcutaneous injection of the pulmonary endothelial toxin, monocrotaline, a marked smooth muscle hypertrophic and hyperplastic response was observed in the mid-sized pulmonary vessels (FIG. 5A). Similiar results were seen in animals transfected with the control vector, pcDNA 3.1 (FIG. 5B). Following cell-based gene transfer of VEGF, a significant decrease in medial thickness and area was observed in vessels of 0 to 90 microns external diameter (FIG. 5C). See also FIG. 6, which shows that a significant attenuation of medial area was detected in those animals treated with monocrotaline and VEGF, as compared to those who received monocrotaline alone or monocrotaline and the null transfected cells (pcDNA 3.1).

Using the viral-based primers, the exogenous VEGF transcript was selectively amplified using the polymerase chain reaction. In this regard, see FIG. 7 which shows that, in animals injected with the VEGF transfected cells, a variable but consistently detectable signal could be detected at the correct size (lanes 1–3), however no signal was detectable in either the monocrotaline alone or control transfected animals (lanes 4 and 5). RNA quality and loading was assessed by amplifying the house-keeping gene GAPDH, which was consistently present in all samples. This demonstrates that the foreign RNA was being transcribed 28 days after cell-based gene transfer and that potentially the presence of the transcript, and presumably the translated protein, was causally related to the lowering of RVSP in the VEGF treated animals.

EXAMPLE 8

Monocrotaline Reversal Studies

To determine if cell-based gene transfer of $VEGF_{165}$ would be capable of reversing or preventing the progression of established pulmonary hypertension in an animal model of disease, six to eight week old Fisher 344 rats were injected subcutaneously with 80 milligrams/kilogram of monocrotaline. Fourteen days after monocrotaline injection the animals were anesthetized and a Millar catheter was passed into the right ventricle and the RV pressure recorded. Pulmonary artery smooth muscle cells transfected with either pVEGF (n=10) or pcDNA 3.1 (n=8) were then injected in aliquots of 500,000 cells into the external jugular vein, and the animals allowed to recover. At 28 days after monocrotaline injection, and 14 days after cell-based gene transfer, the animals were reanesthetized, and a Millar microtip catheter reinserted via the right internal jugular vein into the right ventricle. The right ventricular systolic pressure (RVSP) was recorded, and the catheter was then inserted into the ascending aorta and the systemic arterial pressure recorded. The animals were then sacrificed and the hearts excised. The RV/LV ratios were determined as an indicator of hypertrophic response to long-standing pulmonary hypertension. The right ventricular systolic pressures and RV/LV ratios were compared between the pVEGF and pcDNA 3.1 groups.

Two weeks after monocrotaline injection, the RVSP was elevated to 27±1 mm Hg. In the animals who received pcDNA 3.1 transfected cells the pressure was further increased to 55±5 mm Hg at four weeks after monocrotaline delivery. However, in the pVEGF treated animals the RVSP had only increased to 37±3 mm Hg (p<0.01). In this regard, see FIG. 8 in which the right ventricular systolic pressure (RVSP) is graphed for the animals injected with the control vector transfected (pcDNA 3.1) and the VEGF transfected smooth muscle cells (pVEGF), 14 days after monocrotaline injection. Four weeks after injection of the pulmonary endothelial toxin monocrotaline, the RVSP was increased to 55 mm Hg in the pcDNA 3.1 group, but was significantly decreased to 37 mm Hg in the pVEGF transfected animals.

The RV/LV ratio was significantly elevated in the pcDNA group to 0.395±0.022, but following VEGF gene transfer the ratio was significantly reduced to 0.278±0.012 (p<0.0005). Again no difference in aortic pressure was noted. In this regard, see FIG. 9, in which the right ventricular to left ventricular plus septal ratio (RV/LV) is graphed for the animals injected with the control vector transfected (pcDNA 3.1) and the VEGF transfected smooth muscle cells (pVEGF), 14 days after monocrotaline injection. Four weeks after injection of monocrotaline, the ratio was increased to 0.395 in the pcDNA 3.1 group, but was significantly decreased to 0.278 in the pVEGF transfected animals.

EXAMPLE 9

Treatment of Primary Pulmonary Hypertension with Nitric Oxide Synthase Introduced by Cell Based Gene Transfer Pulmonary artery smooth muscle cells (SMC) were harvested from Fisher 344 rats, and transfected in vitro with the full-length coding sequence for endothelial nitric oxide synthase (eNOS) under the control of the CMV enhancer/promoter. 13 syngenetic rats were injected with 80 mg/kg of monocrotaline subcutaneously, and of these, 7 were randomized to receive eNOS transfected SMC ($5 \times 10^5$) via the jugular vein. 28 days later right ventricular (RV) pressure was measured by means of a Millar micro-tip catheter and pulmonary histology examined.

ENOS gene transfer significantly reduced systolic RV pressure from 52+/−6 mm Hg in control animals (monocrotaline alone, n=6) to 33+/−7 in the eNOS treated animals (n=7, p=0.001). Similarly, RV diastolic pressures were reduced from 15+/−7 mm Hg in the controls, to 4+/−3 in the eNOS treated animals (p=0.0055). In addition, there was a significant attenuation of the vascular hypertrophy and neomuscularization of small vessels in the animals treated with eNOS.

Cell-based gene transfer of the nitric oxide synthase to the pulmonary vasculature is thus an effective treatment strategy in the monocrotaline model of PPH. It offers a novel approach with possibilities for human therapy.

Statistical Analysis

Data are presented as meansistandard error of the mean. Differences in right ventricular pressures, RVILV ratios, and medial area in the pVEGF, pcDNA 3.1, and monocrotaline transfected animals were assessed by means of an analysis of variance (ANOVA), with a post-hoc analysis using the Bonferroni correction, for the prevention experiments. Unpaired tests were used to compare differences in right ventricular pressures and RV/LV ratios in the pVEGF and pcDNA 3.1 treated animals, for the reversal experiments. Differences in the number of fluorescently labeled cells or transfected cells over time were assessed by means of an analysis of variance (ANOVA), with a post-hoc analysis using a Fisher's Protected Least Significant Difference test. In all instances, a value of p<0.05 was accepted to denote statistical significance.

EXAMPLE 10

Skin Fibroblast Explant Culture

Fisher 344 rats (Charles River Co.) were obtained at 21 days of age and were sacrificed by overdose with ketamine and xylazine. The hair was carefully shaved and the back skin was excised and transferred immediately into a phosphate-buffered saline (PBS) solution containing 2% penicillamine and streptomycin (Gibco BRL, Burlington, Ontario). The epidermal and deep fat and connective tissue was removed using a scalpel. The dermal tissue was cut into approximately 4 millimeter square pieces which were placed on individual fibronectin-coated (Sigma Chemical Co., Mississauga, Ontario) tissue culture plates (Falcon, Becton Dickinson Canada, Mississauga, Ontario). The explants were then grown in Dulbecco's Modified Eagle Media with 20% fetal calf serum (FCS) and 2% penicillamine and streptomycin (all Gibco BRL), in a humidified environment with 95% $O_2$ and 5% $CO_2$ at 37° C., with the media being changed every second day. Explants were passaged using 0.05% trypsin/EDTA (Gibco BRL) once many thin, spindle-shaped cells could clearly be seen growing from the dermal explant and the remaining explanted tissue was removed. The cells were then grown in DMEM with 20% FCS and 2% penicillamine and streptomycin until they were to be used in further experiments.

The purity of the cells as to effective type was checked, using antibodies and standard staining techniques, to determine the approximate number of available, effective cells of fibroblast lineage.

Fluorescent cell labeling of the cells was conducted as described in Example 1, followed by in vitro experiments to determine fluorescence, also as described in Example 1.

EXAMPLE 11

Ex Vivo Fibroplast Cell Transfection with the CMV-βGal Plasmid

The vector CMV-βGal (Clontech Inc., Palo Alto, Calif.), which contains the beta-galactosidase gene under the control of the cytomegalovirus enhancer/promoter sequence, was used as a reporter gene to follow the course of in vivo transgene expression. Fibroblasts were grown to 70 to 80% confluence. The optimal ratio of liposome to DNA was determined to be 6 μg of liposome/1 μg of DNA. Cells were washed with DMEM medium (no additives) and 6.4 mls of DMEM was added to each 100 mm plate. 200 μl of Genefector (Vennova Inc., Pablo Beach Fla.) was diluted in 0.8 mls of DMEM and mixed with 16 μg of DNA (CMV-βgal) also diluted in 0.8 ml of DMEM. The liposome solution was then added dropwise over the entire surface of the plate, which was gently shaken and incubated at 30° C. for eight hours. This method was used to avoid the use of viral vectors and simultaneously obtain significant in vitro transfection efficiencies. The Genefector product is an optimized liposome preparation. This Genefector-DNA complex then interacts with cell surface and is transported into the cytoplasm, after which the plasmid DNA can translocate to the nucleus.

Then the transfection medium was replaced with 20% FBS, with 2% penicillin/streptomycin in M199 media and incubated for 24 to 48 hours. This method resulted in transfection efficiencies between 40 and 60%.

EXAMPLE 12

Animal Surgery and Detection of Fluorescently-Labeled Cells in tissue

Animal surgery followed by introduction of dermal fibroblast cells labeled with CMTMR or transfected with plasmid vector CMV-βgal, was conducted as described in Examples 4 and 5, and the fluorescently labeled fibroblast cells in tissue were similarly detected.

At 30 minutes or 24 hours after delivery of labeled cells (n=3 for each time-point), or saline injection (negative control, n=3), the animals were sacrificed by anesthetic overdose, and the chest cavity was opened. The pulmonary artery and trachea were flushed with saline, and the right and left lungs excised. Transverse slices were taken from the basal, medial and apical segments of both lungs, and specimens obtained from the liver, spleen, kidney and gastronemius muscle. Tissue specimens were embedded in OCT compound (Sakura Finetek U.S.A. Inc., Torrance, Calif.) en face, and then flash frozen in liquid nitrogen. Ten micron sections were cut from these frozen blocks at 2 different tissue levels separated by at least 200 microns, and these sections were then examined under a fluorescent microscope using a rhodamine filter, and the number of intensely fluorescing cells was counted in each en face tissue specimen.

The estimate of the total number of labeled cells present within the entire lung was obtained as described in Example 5.

30 minutes after fibroblast delivery, 373±36 CMTMR-labeled cells/cm$^2$ were identified within the lung sections, which represented approximately 60% of the total number of cells injected. After 24 hours there was only a slight decrease in CMTMR-labeled cells to 317±4/cm$^2$ or 85% of the 30-minute value, indicating excellent survival of transplanted cells. The survival of CMTMR-labeled cells at later time points of 2, 4, 7, and 14 days and 1, 2, 3 and 6 months are also evaluated to establish the time course of transplanted cell survival in the lungs of recipient rats. No brightly fluorescent signals were seen in any of the lungs injected with non-labeled smooth muscle cells.

In the spleen, liver and skeletal muscle tissue no fluorescent signals were identified. In 2 out of 4 kidneys examined, irregular fluorescent signals could be identified. None of these appeared to conform to the shape of a whole cell, and were presumed to represent those cells that were sheared or destroyed during cell injection or shortly thereafter. In addition, no fluorescent signals were identified in any organ outside of the lung 7 days after injection.

EXAMPLE 13

Monocrotaline Prevention Studies with Transfected Dermal Fribroblasts

The procedure of Example 7 was largely repeated to determine if cell-based gene transfer of $VEGF_{165}$ in dermal fibroblasts would be capable of inhibiting the development of pulmonary hypertension in an animal model of the disease, dermal fibroblasts which had been transfected with either pVEGF or pcDNA 3.1 (an empty vector) were prepared as described above. The full-length coding sequence of $VEGF_{165}$ was generated by performing a reverse transcription polymerase chain reaction using total RNA extracted from human aortic smooth muscle cells and the following sequence specific primers: sense 5' TCGGGC-CTCCGAAACCATGA 3', (SEQ. ID. No. 7) antisense 5' CCTGGTGAGAGATCTGGTTC 3' (SEQ. ID. No. 8). This generated a 649 bp fragment which was cloned into the PGEM-T vector (Promega, Madison, Wis.), and sequenced to confirm identity. The fragment was then cloned into the expression vector pcDNA 3.1 at the EcoR1 restriction site, and correct orientation determined using a differential digest. The insert deficient vector (pcDNA 3.1) was used as a control for the monocrotaline experiments. All plasmid DNA was introduced into a JM109 strain of E. Coli via the heat-shock method of transformation, and bacteria were cultured overnight in LB media containing 100 micrograms/millilitre of ampicillin. The plasmid was then purified using an endotoxin-free purification kit according to the manufacturer's instructions (Qiagen Endotoxin-Free Maxi Kit, Qiagen Inc., Mississauga, Ontario), producing plasmid DNA with an $A_{260}/A_{280}$ ratio of greater than 1.75, and a concentration of at least 1.0 micrograms/microliter.

Transfected dermal fibroblasts were trypsinized and divided into aliquots of 500,000 cells. Six to eight week old Fisher 344 rats were then anesthetized and injected subcutaneously with either 80 milligrams/kilogram of monocrotaline (n=13) (Aldrich Chemical Co., Milwaukee, Wis.) alone, or with monocrotaline and, via a catheter in the external jugular vein, either 500,000 pVEGF (n=5), or pcDNA 3.1 (n=3) transfected cells.

Following the procedure described in Example 7, the vein was tied off, the incision closed in the normal fashion, and the animals allowed to recover. At 28 days after injection, animals were re-anesthetized, and a Millar microtip catheter reinserted via the right internal jugular vein into the right ventricle. The right ventricular systolic pressure was recorded, and the catheter was then inserted into the ascending aorta and the systemic arterial pressure recorded. The animals were then sacrificed and the hearts excised. The right ventricular (RV) to left ventricular plus septal (LV) weight ratios (RV/LV ratio) were determined as an indicator of hypertrophic response to long-standing pulmonary hypertension. Lungs were flushed via the pulmonary artery with sterile phosphate-buffered saline, and were gently insufflated with 2% paraformaldehyde via the trachea. Pulmonary segments were then either snap frozen in liquid nitrogen for subsequent RNA extraction, or were fixed via immersion in 2% paraformaldehyde for paraffin embedding and sectioning. The right ventricular systolic pressures and RV/LV ratios were compared between the pVEGF, pcDNA 3.1, and monocrotaline alone groups.

RNA extracted from rat lungs was quantified, and 5 micrograms of total RNA from each animal was reverse transcribed using the murine moloney leukemia virus reverse-transcriptase, and an aliquot of the resulting cDNA was amplified with the polymerase chain reaction (PCR) using the following sequence-specific primers: sense 5' CGCTACTGGCTTATCGAAATTMTACGACTCAC 3' (SEQ. ID No. 3), antisense 5' GGCCTTGGTGAG-GTTTGATCCGCATMT3' (SEQ. ID. No. 4), for 30 cycles with an annealing temperature of 65° C. Ten microlitres of a fifty microlitre reaction were run on a 1.5% agarose gel. The upstream primer was located within the T7 priming site of the pcNDA 3.1 vector and therefore should not anneal with any endogenous RNA transcript, and the downstream primer was located within exon 4 of the coding region of VEGF. Therefore, the successful PCR reaction would selectively amplify only exogenous VEGF RNA. To control for RNA quantity and quality, a second aliquot of the same reverse transcription reaction was amplified with the following primers for the constitutively-expressed gene GAPDH: sense 5' CTCTMGGCTGTGGGCMGGTCAT 3' (SEQ. ID. No. 5), antisense 5' GAGATCCACCACCCTGT-TGCTGTA 3' (SEQ. ID. No. 6). This reaction was carried out for 25 cycles with an annealing temperature of 58° C. Ten microlitres of a fifty microfiltre reaction were run on a 1.5% agarose gel, and compared to the signal obtained from the VEGF PCR.

Paraformaldehyde fixed rat lungs were cut perpendicular to their long axis and were paraffin-embedded en face. Sections were obtained and stained using the elastin-von Giessen's (EVG) technique. The sections were assessed by a blinded observer who measured all vessels with a perceptible media within each cross-section under 40× magnification using the C+ computer imaging system. The medial area of each vessel was determined and an average was obtained for each vessel size from 0 to 30, 30 to 60, 60 to 90, 90 to 120, and greater than 120 microns in external diameter, for each animal. The averages from each size were compared between the pVEGF, pcDNA 3.1, and monocrotaline alone groups.

Four weeks following monocrotaline injection (n=11) alone, the right ventricular systolic pressure was increased to 48±2 mm Hg, and there was no improvement in those animals who received the pcDNA 3.1 transfected cells (n=3) with the average RVSP remaining at 48±2 mm Hg. However, in those animals treated with the pVEGF transfected fibroblasts (n=5) the RV pressure was significantly decreased to 32±2 mm Hg (p<0.0001).

As anticipated from the long-standing pulmonary hypertension, the RV/LV ratio was significantly elevated from baseline following monocrotaline injection (n=13) to 0.345±0.015 and was very similar in the pcDNA 3.1 transfected group (n=3). Following VEGF gene transfer (n=5) the ratio was significantly lower than the pcDNA 3.1 transfected group. No difference in aortic pressure was noted. Four weeks after injection of the pulmonary endothelial toxin monocrotaline and transfected cells, the RV/LV ratio is significantly elevated in the MCT group and in the pcDNA 3.1 group, but was lower in the pVEGF transfected animals.

Morphometric analysis of the tissue sections revealed that in both the monocrotaline alone and the pcDNA 3.1 treated groups, the medial area for the vessel groups from 0 to 30, 30 to 60 and 60 to 90 microns was significantly increased, as compared to the VEGF treated animals. Similar results were seen in animals transfected with the control vector, pcDNA 3.1. Following cell-based gene transfer of VEGF, a significant decrease in medial thickness and area was observed in vessels of 0 to 90 microns external diameter.

Using the plasmid-based primers, the exogenous VEGF transcript was selectively amplified using the polymerase chain reaction. RNA quality and loading was assessed by amplifying the house-keeping gene GAPDH, which was consistently present in all samples. This demonstrated that the foreign RNA was being transcribed 28 days after cell-based gene transfer and that potentially the presence of the transcript, and presumably the translated protein, was causally related to the lowering of RVSP in the VEGF treated animals.

Blood taken from the animals by left ventricular puncture immediately before sacrifice was analyzed for pH, oxygen loading (pO2), carbon dioxide loading (pCO2) and % saturation. The results are given below.

Blood Analysis Data

|  | pH | pCO2 | pO2 | % Sat'n |
|---|---|---|---|---|
| VEGF/fibroblast transfected animals | | | | |
| Mean (of 5 animals) | 7.374 | 51.2 | 78.3 | 86.58 |
| Standard deviation, SD | 0.0502 | 5.699 | 17.89 | 9.867 |
| pcDNA/fibroblast transfected animals | | | | |
| Mean (of 3 animals) | 7.35 | 58.333 | 60.8 | 74.4 |
| SD | 0.02 | 3.761 | 7.615 | 7.882 |

These results indicate preliminarily that arterial $O_2$ tension and saturation are better in the VEGF transfected group than in animals receiving null-transfected cells. This is consistent with the improvement in pulmonary hemodynamics and lung vascular morphology, and argues against significant right to left shifting as might occur in pulmonary arterial to venous shunts.

The creation of "shunting"—formation of new passageways between the arteries and the capillaries of the pulmonary system, by-passing the veins and thereby limiting the blood oxygen up-take, does not occur to any problematic extent, according to preliminary indications.

DISCUSSION

The present invention represents evidence of successful non-viral gene transfer to the pulmonary vasculature using various types of transfected cells e.g. smooth muscle cells and dermal fibroblasts, and provides a demonstration of potential therapeutic efficacy of an angiogenic strategy in the treatment of PH using this approach. This method of delivery was associated with a high percentage of cells being retained within the lung at 48 hours, as determined by both the fluorescence labeling technique and by the reporter gene studies using beta-galactosidase, and with moderate but persistent gene expression over 14 days. These results roughly parallel what has previously been demonstrated with a viral-based method of intravascular gene delivery to the pulmonary vasculature (see Schachtner, S. K., J. J. Rome, R. F. Hoyt, Jr., K. D. Newman, R. Virmani, D. A. Dichek, 1995. In vivo adenovirus-mediated gene transfer via the pulmonary artery of rats. Circ. Res. 76:701–709; and Rodman, D. M., H. San, R. Simari, D. Stephan, F. Tanner, Z. Yang, G. J. Nabel, E. G. Nabel, 1997. In vivo gene delivery to the pulmonary circulation in rats: transgene distribution and vascular inflammatory response. Am. J. Respir. Cell Mol. Biol. 16:640–649).

However, the cell-based technique provided by the present invention avoids the use of a potentially immunogenic viral construct, was not associated with any significant pulmonary or systemic inflammation, and permits more selective transgene expression within the pulmonary microvasculature, and in particular the targeting of transgene expression localized to the distal pulmonary arteriolar region, which is primarily responsible for determining pulmonary vascular resistance, and therefore PH.

The present invention addresses several key questions related to the feasibility of a cell-based gene transfer approach for the pulmonary circulation, including the survival of genetically engineered cells and the selectivity of their localization and transgene expression within the lungs. As demonstrated above in Example 6, implanted cells were efficiently retained by the lungs.

The finding that most of the cells appeared to lodge within small pulmonary arterioles is consistent with the normal physiological role the lung plays as an anatomical filter, and thus it would be expected that relatively large particles such as resuspended cells would become lodged within the pulmonary microvasculature. However, this 'targeting' of cells to the pre-capillary resistance vessel bed in a highly selective manner may prove very useful in the treatment for certain pulmonary vascular disorders. The overexpression of a vasoactive gene at the distal arteriolar level could provide a highly localized effect in a vascular region critical in the control of pulmonary vascular resistance and could amplify the biological consequences of gene transfer. In fact, the localized reduction in RVSP seen in monocrotaline-treated animals receiving VEGF transfected cells, occurred without a corresponding decrease in systemic pressures, highlighting the specificity of this method of transfection. This approach may therefore offer significant advantages over other pulmonary selective gene transfer strategies such as endotracheal gene delivery, which results in predominantly bronchial overexpression, or catheter-based pulmonary vascular gene transfer, which produces diffuse macrovascular and systemic overexpression (see Rodman, D. M., H. San, R. Simari, D. Stephan, F. Tanner, Z. Yang, G. J. Nabel, E. G. Nabel, 1997. In vivo gene delivery to the pulmonary circulation in rats: transgene distribution and vascular inflammatory response. Am. J. Respir. Cell Mol. Biol. 16:640–649; and Nabel, E. G., Z. Yang, D. Muller, A. E. Chang, X. Gao, L. Huang, K. J. Cho, G. J. Nabel, 1994. Safety and toxicity of catheter gene delivery to the pulmonary vasculature in a patient with metastatic melanoma. Hum. Gene Ther. 5:1089–1094).

This significant effect occurred despite an overall relatively low mass of organ-specific transfection, and was likely due to the fact that the transfected cells were targeted, based on their size, to the precapillary pulmonary resistance vessels which play a critical role in controlling pulmonary pressure. This method of pulmonary vascular gene transfer may have benefits over existing techniques by minimizing the overall "load" of foreign transgene that is delivered to the body and may thereby theoretically reduce the incidence of undesired side-effects.

I claim:

1. A process of inhibiting progression of a pulmonary disorder treatable by an angiogenic or vasodilator factor in a mammalian patient suffering from said pulmonary disorder by conducting gene therapy which comprises administration to the lung by injection into the venous side of the circulatory system of the mammalian patient of viable, transfected autologous mammalian cells, wherein said transfected mammalian cells express at least one angiogenic or vasodilator transgene.

2. The process according to claim 1 wherein the mammalian cells are dermal fibroblasts, smooth muscle cells or endothelial cells.

3. The process according to claim 1 wherein the transfected cells contain a transgene coding for an angiogenic factor.

4. The process according to claim 1 wherein the angiogenic factor is selected from the group consisting of, vascularendothelial growth factor, fibroblastgrowth factor, angiopoietin-1, transforming growth factor-β, hepatic growth factor (scatter factor) and hypoxia inducible factor (HIF).

5. The process according to claim 4 wherein the angiogenic factor is vascular endothelial growth factor, VEGF.

6. The process according to claim 1 wherein the transfected cells contain a trans-gene coding for a hormone.

7. The process according to claim 1 wherein the transfected cells contain a transgene coding for nitric oxide synthase.

8. The process according to claim 5 wherein the hormone is selected from the group consisting of growth hormone, insulin, and thyroid stimulating hormone (TSH).

* * * * *

UNITED STATES PATENT AND TRADEMARK OFFICE
CERTIFICATE OF CORRECTION

PATENT NO.    : 6,482,406 B1
DATED         : November 19, 2002
INVENTOR(S)   : Duncan J. Stewart It is certified that error appears in the above-identified patent and that said Letters Patent is hereby corrected as shown below:

Title page,
Item [56], OTHER PUBLICATIONS, delete "Teichart-Kuliszewaska et al", insert -- Babaei et al --.
Delete "Flqui et al., hum Gene. Ther. 1999, Reversal of diabetes in mice by implantation of human fibroblast genetically engineered to release mature human insulin"."
Delete "Babie", insert -- Babaei --.
Delete "Feman, Curr. Opin Opthalmol, 1997, "New Discoveries in diabetes – and thyroid-related eye disease"."
"Takeshita et al." delete "NDA", insert -- DNA --.
Page 3, right hand column, lines 8 to 9, delete "hyper-tension"." and, insert -- hyper-tension --, Abstracts from the 69th Scientific Sessions, American Heart Association, New Orleans, Louisiana, Nov. 10-13, 1996. --.

Column 1,
Line 29, following "mammalian cell," insert -- or --;
Line 32, delete "Then the cells", insert -- The cells --;
Line 38, following "to be transferred", insert -- , --.

Column 6,
Lines 20 and 31, delete "arteriols", insert -- arterioles --;

Column 8,
Line 34, delete "ex vivi", insert -- ex vivo --.

Column 9,
Line 8, delete "(SEQ ID. No.1)antisense", insert -- (SEQ ID. No.1) antisense --.

Column 10,
Line 20, delete "excise", insert -- excess --.

Column 16,
Line 23, delete "meansistandard", insert -- means and standard --;
Line 24, delete "RVILV", insert -- RVLV --.

UNITED STATES PATENT AND TRADEMARK OFFICE
CERTIFICATE OF CORRECTION

PATENT NO. : 6,482,406 B1
DATED : November 19, 2002
INVENTOR(S) : Duncan J. Stewart It is certified that error appears in the above-identified patent and that said Letters Patent is hereby corrected as shown below:

Column 20,
Line 5, delete "ratio is", insert -- ratio was --;
Between lines 40 and 41, insert a blank line.

Signed and Sealed this

Twelfth Day of August, 2003

JAMES E. ROGAN
*Director of the United States Patent and Trademark Office*